United States Patent
Chi et al.

(10) Patent No.: US 11,779,905 B2
(45) Date of Patent: Oct. 10, 2023

(54) CATALYST COMPOSITIONS AND PROCESS FOR DIRECT PRODUCTION OF HYDROGEN CYANIDE IN AN ACRYLONITRILE REACTOR FEED STREAM

(71) Applicant: Ascend Performance Materials Operations LLC, Houston, TX (US)

(72) Inventors: Yawu T. Chi, Sugar Land, TX (US); Scott G. Moffatt, Pearland, TX (US); Mikhail Khramov, Pensacola, FL (US); Ranjeeth Reddy Kalluri, Friendswood, TX (US); Bruce F. Monzyk, Town Creek, AL (US); Soundar Ramchandran, Friendswood, TX (US); Marty Alan Lail, Raleigh, NC (US); Maruthi Sreekanth Pavani, Kavali (IN)

(73) Assignee: Ascend Performance Materials Operations LLC, Houston, TX (US)

(*) Notice: Subject to any disclaimer, the term of this patent is extended or adjusted under 35 U.S.C. 154(b) by 282 days.

(21) Appl. No.: 17/162,170

(22) Filed: Jan. 29, 2021

(65) Prior Publication Data
US 2021/0146339 A1    May 20, 2021

Related U.S. Application Data

(62) Division of application No. 16/068,505, filed as application No. PCT/US2017/012671 on Jan. 9, 2017.
(Continued)

(51) Int. Cl.
*B01J 23/00* (2006.01)
*B01D 53/86* (2006.01)
(Continued)

(52) U.S. Cl.
CPC ........ *B01J 23/002* (2013.01); *B01D 53/8634* (2013.01); *B01D 53/94* (2013.01);
(Continued)

(58) Field of Classification Search
CPC ........ B01J 23/002; B01J 21/04; B01J 21/063; B01J 21/066; B01J 21/08; B01J 23/8876;
(Continued)

(56) References Cited

U.S. PATENT DOCUMENTS

| 4,142,994 A | 3/1979 | Alafandi |
| 4,511,548 A | 4/1985 | Attig et al. |

(Continued)

FOREIGN PATENT DOCUMENTS

| CN | 101066528 B | ‡ | 9/2010 |
| CN | 101066528 B |  | 9/2010 |

(Continued)

OTHER PUBLICATIONS

European Search Report Issued in Counterpart European Patent Application No. 17736498.1 dated Jul. 9, 2019.
(Continued)

*Primary Examiner* — James A Fiorito
(74) *Attorney, Agent, or Firm* — COZEN O'CONNOR

(57) ABSTRACT

The present invention relates to catalyst compositions containing a mixed oxide catalyst of formula (I) or formula (II) as described herein, their preparation, and their use in a process for ammoxidation of various organic compounds to their corresponding nitriles and to the selective catalytic oxidation of excess $NH_3$ present in effluent gas streams to $N_2$ and/or $NO_x$.

16 Claims, 12 Drawing Sheets

101. Propylene/Propane/CH₃OH
102. Ammonia
103. Air
104. Fluidized bed AN reactor as a primary reactor
105. AN product stream
106. CH₃OH (Liquid/Vapor)
107. Secondary reactor
108. Product gas with NH₃ removed and/or enriched in HCN
109. Product gas cooler
110. Cooled product gas
111. Quencher system
112. Sulfuric acid
113. Waste water
114. AN/HCN Recovery system
115. Crude ACN (Optional)
116. Absorber effluent stream
117. AN/HCN Purification system
118. HCN product
119. AN product
120. Heavies Purge

Related U.S. Application Data

(60) Provisional application No. 62/276,861, filed on Jan. 9, 2016.

(51) Int. Cl.

| | | |
|---|---|---|
| *B01J 37/03* | (2006.01) | |
| *B01J 37/04* | (2006.01) | |
| *B01J 23/887* | (2006.01) | |
| *B01J 23/889* | (2006.01) | |
| *B01J 23/89* | (2006.01) | |
| *B01J 35/10* | (2006.01) | |
| *B01D 53/94* | (2006.01) | |
| *B01J 21/04* | (2006.01) | |
| *B01J 21/06* | (2006.01) | |
| *B01J 21/08* | (2006.01) | |
| *B01J 37/02* | (2006.01) | |
| *C07C 253/24* | (2006.01) | |

(52) U.S. Cl.
CPC ............. *B01J 21/04* (2013.01); *B01J 21/063* (2013.01); *B01J 21/066* (2013.01); *B01J 21/08* (2013.01); *B01J 23/8876* (2013.01); *B01J 23/8878* (2013.01); *B01J 23/8898* (2013.01); *B01J 23/8993* (2013.01); *B01J 35/1009* (2013.01); *B01J 35/1019* (2013.01); *B01J 37/0215* (2013.01); *B01J 37/031* (2013.01); *B01J 37/04* (2013.01); *C07C 253/24* (2013.01); *B01D 2251/102* (2013.01); *B01D 2255/1026* (2013.01); *B01D 2255/209* (2013.01); *B01D 2255/2047* (2013.01); *B01D 2255/2065* (2013.01); *B01D 2255/2073* (2013.01); *B01D 2255/2096* (2013.01); *B01D 2255/2098* (2013.01); *B01D 2255/20738* (2013.01); *B01D 2255/20746* (2013.01); *B01D 2255/20753* (2013.01); *B01D 2255/20761* (2013.01); *B01D 2255/20769* (2013.01); *B01D 2255/20784* (2013.01); *B01D 2255/20792* (2013.01); *B01D 2255/40* (2013.01); *B01D 2255/9202* (2013.01); *B01D 2255/9207* (2013.01); *B01D 2257/406* (2013.01); *B01J 2523/00* (2013.01); *B01J 2523/18* (2013.01); *B01J 2523/19* (2013.01); *B01J 2523/44* (2013.01); *B01J 2523/67* (2013.01); *B01J 2523/68* (2013.01); *B01J 2523/69* (2013.01); *B01J 2523/72* (2013.01); *B01J 2523/74* (2013.01); *B01J 2523/824* (2013.01); *B01J 2523/828* (2013.01)

(58) Field of Classification Search
CPC .......... B01J 23/8878; B01J 23/8898; B01J 23/8993; B01J 35/1009; B01J 35/1019; B01J 37/0215; B01J 37/031; B01J 37/04; C07C 253/24; C01D 53/8634; C01D 53/94
See application file for complete search history.

(56) References Cited

U.S. PATENT DOCUMENTS

| | | | |
|---|---|---|---|
| 5,082,819 A | 1/1992 | Boeck et al. | |
| 5,198,580 A ‡ | 3/1993 | Bartek | ............... C07C 45/33 562/549 |
| 5,446,004 A ‡ | 8/1995 | Tenten | ............. B01J 23/8885 502/328 |
| 6,667,020 B2 ‡ | 12/2003 | Seely | ............. C01C 3/0212 423/376 |
| 6,888,024 B2 ‡ | 5/2005 | Dieterle | ............. B01J 23/002 562/546 |
| 8,822,371 B2 * | 9/2014 | Raichle | ............. B01J 35/023 502/340 |
| 8,835,666 B2 ‡ | 9/2014 | Brazdil, Jr. | ......... B01J 23/8878 558/324 |
| 8,877,964 B2 ‡ | 11/2014 | Nakazawa | ............ B01J 35/04 562/535 |
| 9,545,610 B2 * | 1/2017 | Simanzhenkov | ....... C07C 7/167 |
| 2002/0198398 A1 | 12/2002 | Paparizos et al. | |
| 2004/0062870 A1 | 4/2004 | Dieterle et al. | |
| 2004/0063989 A1 | 4/2004 | Hechler et al. | |
| 2005/0033093 A1 | 2/2005 | Teshigahara et al. | |
| 2007/0021630 A1‡ | 1/2007 | Liang | ............... C07C 51/252 562/535 |
| 2011/0218352 A1 | 9/2011 | Besecker et al. | |
| 2013/0072710 A1 | 3/2013 | Brazdil et al. | |
| 2015/0343427 A1 | 12/2015 | Brazdil, Jr. et al. | |

FOREIGN PATENT DOCUMENTS

| | | | | |
|---|---|---|---|---|
| CN | 102892497 A ‡ | 1/2013 | ............ | B01J 23/002 |
| CN | 102892497 A | 1/2013 | | |
| EP | 0076678 A2 | 4/1983 | | |
| WO | 2015/183284 A1 | 12/2015 | | |

OTHER PUBLICATIONS

International Search Report Issued in Corresponding International Patent Application No. PCT/US2017/012671 dated May 8, 2017.
Written Opinion Issued in Corresponding International Patent Application No. PCT/US2017/012671 dated May 8, 2017.

\* cited by examiner
‡ imported from a related application

Figure 1

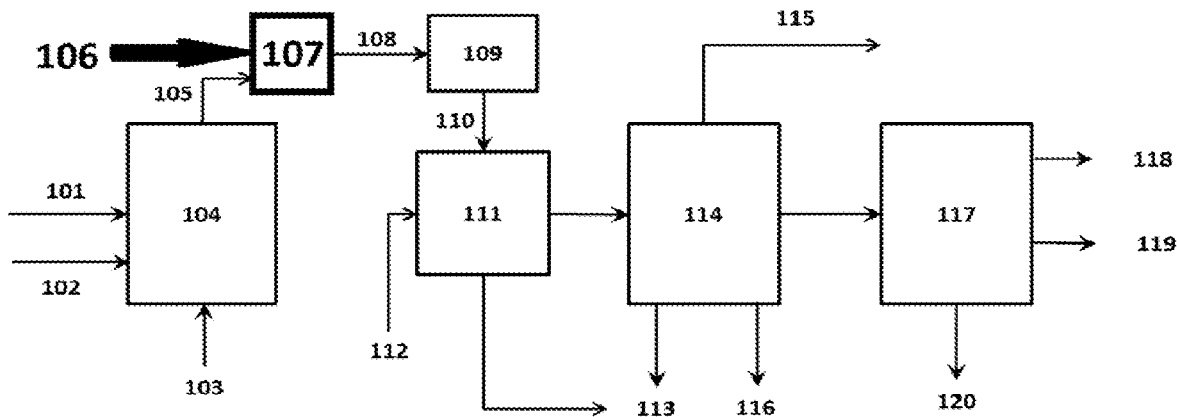

101. Propylene/Propane/CH₃OH
102. Ammonia
103. Air
104. Fluidized bed AN reactor as a primary reactor
105. AN product stream
106. CH₃OH (Liquid/Vapor)
107. Secondary reactor
108. Product gas with NH₃ removed and/or enriched in HCN
109. Product gas cooler
110. Cooled product gas
111. Quencher system
112. Sulfuric acid
113. Waste water
114. AN/HCN Recovery system
115. Crude ACN (Optional)
116. Absorber effluent stream
117. AN/HCN Purification system
118. HCN product
119. AN product
120. Heavies Purge

CATALYST COMPOSITIONS AND PROCESS FOR DIRECT PRODUCTION OF HYDROGEN CYANIDE IN AN ACRYLONITRILE REACTOR FEED STREAM

CROSS-REFERENCE TO RELATED APPLICATIONS

The present application is division of U.S. Ser. No. 16/068,505, which is a U.S. National Stage of International Application No. PCT/US2017/012671, filed Jan. 9, 2017, which claims the benefit of Provisional Patent Application No. 62/276,861 filed Jan. 9, 2016, the entire disclosures of which are relied on for all purposes and is incorporated into this application by reference.

BACKGROUND OF THE INVENTION

Hydrogen cyanide (HCN) and acetonitrile (ACN) have long been recognized as un-optimized co-products in the manufacture of acrylonitrile (AN) by the SOHIO process (U.S. Pat. No. 2,904,580), and related synthetic routes that utilize propylene/propane, oxygen ($O_2$), and ammonia ($NH_3$) as feed stocks in an ammoxidation reaction conducted in catalytic fluidized bed reactors. In view of the growing demand for HCN in the past decade and with continued growth predicted in the foreseeable future due to the conversion of HCN to a number of industrial products (e.g., sodium and potassium cyanides for the mining industry, chelating agents, etc.), the demand for acetonitrile also continues to grow in pharmaceutical and in analytical applications. HCN and ACN formation may be expressed by the following reactions in the propylene ($CH_2$=CH—$CH_3$) ammoxidation process:

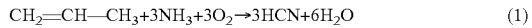

$$CH_2=CH-CH_3 + 3NH_3 + 3O_2 \rightarrow 3HCN + 6H_2O \quad (1)$$

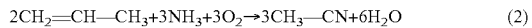

$$2CH_2=CH-CH_3 + 3NH_3 + 3O_2 \rightarrow 3CH_3-CN + 6H_2O \quad (2)$$

Methods for co-producing HCN from AN reactors or for producing HCN directly from low carbon alcohols are well known. The amount of HCN produced as a by-product in propylene ammoxidation is linked to the amount of produced AN. When HCN demand exceeds the production of HCN in a propylene ammoxidation process, methanol ($CH_3OH$) can be fed with propylene into the ammoxidation reactors, where it reacts with $NH_3$ and $O_2$ in the presence of an AN catalyst to produce HCN as follows:

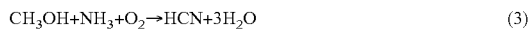

$$CH_3OH + NH_3 + O_2 \rightarrow HCN + 3H_2O \quad (3)$$

However, AN catalysts and reactors are optimized for propylene ammoxidation rather than for $CH_3OH$ ammoxidation to produce HCN. Also, the introduction of $CH_3OH$ into the propylene ammoxidation feed may have the adverse effect of reducing the lifetime of the catalyst. These methods typically involve, for example, the addition (such as by injection) of $CH_3OH$ or other alcohols into an AN reactor; the use of on-purpose $CH_3OH$-to-HCN reactors; the addition of a set of internals within the AN reactor (U.S. Pat. No. 6,716,405); $CH_3OH$-to-HCN process patents, especially as they relate to AN plants; processes for eliminating waste material during the manufacture of AN (U.S. Pat. Nos. 5,288,473; 5,457,723; 5,466,857; and 5,288,473); and processes for the recovery and recycling of $NH_3$ from a vapor stream (U.S. Pat. No. 7,326,391).

The injection of $CH_3OH$ or ethanol (EtOH) into a fluid bed reactor to produce HCN or ACN is well known and minimizes the amount of unconverted $NH_3$ residing in the effluent streams. In addition, the conventional art discloses that $CH_3OH$ or EtOH may be introduced into a fluid bed reactor to increase the amount of co-product (HCN or ACN) while manufacturing AN. For example, U.S. Pat. Nos. 3,911,089; 4,485,079; and 5,288,473 are directed to the ammoxidation of $CH_3OH$ to produce HCN by injection of the $CH_3OH$ into a fluid bed reactor containing an ammoxidation catalyst suitable for the manufacture of acrylonitrile. Each of these patents teaches that $CH_3OH$ injection can be made simultaneously in AN reactors.

Japanese Patent Applications 74-87,474; 79-08, 655; and 78-35,232 relate to methods of increasing HCN yield during the manufacture of AN. Japanese Patent Application 2[1990]-38,333 is directed to improving ACN yields by injecting acetone and/or EtOH during the manufacture of AN. Each of these disclosures is concerned with the production of either additional HCN or ACN within an AN reactor, and are therefore limited by the AN reaction catalyst, the reactor design and/or operational constraints (e.g., excess $O_2$ requirements, optimum feed ratios, etc.).

Metal oxide catalysts have been disclosed as generating HCN from $CH_3OH$ ammoxidation, such as Mo—P oxides (U.S. Pat. No. 2,746,843); Fe—Mo oxides (U.S. Pat. No. 4,425,260); and Mn—P oxides (U.S. Pat. No. 4,457,905). The activities and selectivities of binary metal oxides have been enhanced by the addition of various elements such as those disclosed in U.S. Pat. No. 4,485,079 (promoted Mo—Bi—Ce oxides); U.S. Pat. No. 4,511,548 (promoted Sb—P oxides); U.S. Pat. No. 4,981,830 (promoted Fe—Sb—P oxides); U.S. Pat. No. 5,094,990 (promoted Fe—Sb—P oxides); U.S. Pat. No. 5,158,787 (promoted Fe—Cu—Sb—P oxides); U.S. Pat. No. 5,976,482 (promoted Fe—Sb—P—V oxides); and U.S. Pat. No. 6,057,471 (promoted Mo oxides and promoted Sb oxides). U.S. Pat. No. 7,763,225 discloses a Mn—P oxide catalyst promoted with K, Ca, Mo, Zn, Fe or mixtures thereof that exhibit a higher HCN yield from $CH_3OH$ ammoxidation.

The catalysts used for co-producing HCN from propylene ammoxidation include promoted U—Sb oxides such as disclosed in U.S. Pat. Nos. 3,816,596; 4,000,178; 4,018,712; 4,487,850; 4,547,484; and 6,916,763; and in WO 2000/072962. Promoted Bi—Mo oxides are disclosed in U.S. Pat. Nos. 5,093,299; 5,212,137; 5,658,842; 5,834,394; and 8,455,838. Promoted Sb—Fe oxides are disclosed in U.S. Pat. No. 5,094,990.

U.S. Pat. No. 4,040,978 discloses a multi-step process for the production of an ammoxidation catalyst that includes individually forming the molybdate of cobalt, nickel, iron and an oxide or salt of bismuth; followed by forming an aqueous slurry of the individual molybdates and bismuth oxide or a salt thereof; separating the solid phase from the slurry; adding silica support material to the slurry resulting from the combined solid phases (precipitates), and calcining the spray-dried slurry to form the catalyst.

U.S. Pat. No. 5,780,664 discloses an ammoxidation catalyst which has been prepared by providing a slurry containing a silica sol and sources of component metallic elements, spray-drying the slurry, followed by calcination. U.S. Pat. No. 6,916,763 discloses a process for preparing a catalyst for the oxidation and ammoxidation of olefins by contacting an aqueous $Sb_2O_3$ slurry with $HNO_3$ and one or more metal compounds to form a first mixture which is substantially free of silica sol; heating and drying the first mixture to form a solid product; and then calcining the solid product to form the catalyst.

There have been continuous advances in $CH_3OH$ and propylene ammoxidation catalysts in the past forty years, particularly with respect to improvements in activity, selectivity, and stability. A low activity catalyst requires a temperature increase to achieve an acceptable conversion, which undesirably decreases the selectivity of the target products and adversely reduces catalyst stability. Catalyst activity typically declines over the operating reaction time, eventually requiring partial or full replacement of the catalyst with fresh or regenerated catalyst. In a commercial operation, an increase in temperature within the operation window is also required to compensate for the catalyst deactivation. Thus, there is a need for an activity-improved catalyst which is capable of reaction at a lower operating temperature, which exhibits higher selectivity, a higher product yield and greater catalyst stability which allows for a wider temperature window in which a commercial plant can operate, and also for longer times between costly maintenance and catalyst replacement. In a particular application, a need exists for a "HCN-on-purpose" efficient catalyst that can utilize an AN reactor effluent stream as an $NH_3$ and $O_2$ source and that employs a low carbon number primary alcohol feed to selectively produce HCN in a commercially acceptable yield.

The commercial utility of a catalytic process is highly dependent upon the cost of the catalyst and the associated chemical conversion process, the conversion of the reactant(s), the yield of the desired product(s), and the stability of the catalyst during commercial operation. An activity-improved catalyst that exhibits higher yields of the desired product(s) can minimize downstream process operations, including the need for product purification and the handling of large recycle streams. Therefore, there exists a strong need to develop not only a new or improved catalyst and a method of making the catalyst for HCN and/or ACN production, but also a more effective means for reusing and/or removing unconverted $NH_3$ in an AN reactor effluent stream. The unconverted $NH_3$ present in an ammoxidation reactor effluent stream may originate from ammoxidation of methane, methanol, propane, propylene, isobutane, isobutylene, their derivatives, or mixtures thereof, to form HCN, acrylonitrile and methacrylonitrile, respectively. The same or different catalyst may also convert the unreacted methane, methanol, propylene, propane, isobutylene, isobutane, their derivatives, or mixtures thereof from a first or precedent reactor and unconverted $NH_3$ and/or $O_2$ present in an ammoxidation reactor effluent stream to HCN, acrylonitrile and methacrylonitrile, respectively.

Selective catalytic oxidation (SCO) of ammonia ($NH_3$) to nitrogen ($N_2$) has been employed as a means for ammonia removal in the presence of a catalyst. Noble metal catalysts allow the oxidation of $NH_3$ to $N_2$ to occur at low temperatures which avoids or minimizes the undesired high temperature formation of NOx. U.S. Pat. Nos. 8,007,735 and 7,410,626 disclose noble metals disposed on a support or substrate as catalysts for this purpose. A need exists for a less expensive non-noble metal catalyst, such as a mixed metal oxide catalyst, for selective oxidization of $NH_3$ to $N_2$ in the presence of $O_2$ at low temperatures.

SUMMARY OF THE INVENTION

An aspect of the present invention generally relates to a novel catalyst composition comprising or consisting of a mixed oxide catalyst of formula (I) or (II) or a mixture thereof, its preparation, and its use in the ammoxidation of alcohols, nitriles, ketones, aldehydes, carboxylic acids, esters, ethers, or mixtures thereof to HCN or to the corresponding nitriles, and also in the selective catalytic oxidation (SCO) of $NH_3$ to $N_2$.

Another aspect of the present invention is directed to a process of adding alcohols, such as $CH_3OH$ and/or EtOH, into an AN reactor effluent stream containing unconverted $NH_3$ and $O_2$ to produce HCN under ammoxidation conditions using the catalyst compositions of the invention as a means for removing the unconverted $NH_3$ from the AN production process.

An exemplary embodiment of the present invention minimizes any potentially negative impact associated with an AN reactor design and its operational constraints by specifically utilizing a dedicated secondary reactor placed downstream of the primary AN reactor, where the features of the secondary reactor are specifically tailored for HCN and/or ACN production and/or $NH_3$ elimination using the catalyst compositions of the present invention.

In an exemplary embodiment, the secondary reactor utilizes a fixed bed type catalyst composition of a desired shape (e.g., crushed particles, spheres, cylindrical extrudates, monoliths, and the like). In another exemplary embodiment, the catalyst compositions of the invention are coated onto a secondary monolith substrate or directly extruded into monolith blocks.

An aspect of the invention is a catalyst composition comprising or consisting of a mixed oxide catalyst composition represented by the following formula (I) or (II):

$$Mo_{12}X^1_aX^2_bX^3_cX^4_dX^5_eX^6_fO_h \quad (I)$$

$$FeMo_iCr_jBi_kM_mN_nQ_qX_xY_yO_r \quad (II)$$

or a mixture of (I) and (II), wherein in formula (I):

$X^1$ is Cr and/or W;

$X^2$ is Bi, Sb, As, P, and/or a rare earth metal;

$X^3$ is Fe, Ru, and/or Os;

$X^4$ is Ti, Zr, Hf, B, Al, Ga, In, Tl, Si, Ge, Sn, and/or Pb;

$X^5$ is Co, Rh, Ir, Ni, Pd, Pt, Cu, Ag, Au, Zn, Cd, Hg, Mn, Re, V, Nb, Ta, Se, and/or Te;

$X^6$ is an alkali earth metal and/or an alkali metal; and where the subscripts a, b, c, d, e, f and h are, respectively, the atomic ratios of $X^1$, $X^2$, $X^3$, $X^4$, $X^5$, $X^6$ elements and oxygen (O), relative to 12 atoms of molybdenum (Mo), where $0 \le a \le 5$;

$0.03 \le b \le 25$;

$0 \le c \le 20$;

$0 \le d \le 200$;

$0 \le e \le 8$;

$0 \le f \le 3$; and h is the number of oxygen atoms required to satisfy the valence requirements of the component elements other than oxygen present in formula (I), where $1 \le c+d+e+f \le 200$;

$0 \le e+f \le 8$; and wherein in formula (II):

M is Ce and/or Sb;

O is La, Pr, Nd, Pm, Sm, Eu, Gd, Tb, Dy, Ho, Er, Tm, Yb, Lu, Ti, Zr, Hf, B, Al, Ga, In, Tl, Si, Ge, Sn, Pb, P, and/or As;

Q is W, Ru, and/or Os;

X is Co, Rh, Ir, Ni, Pd, Pt, Cu, Ag, Au, Zn, Cd, Hg, Mn, Re, V, Nb, Ta, Se, and/or Te;

Y is an alkali earth metal and/or an alkali metal; and the subscripts i, j, k, m, n, q, x, y and r are, respectively, the atomic ratios of molybdenum (Mo), chromium (Cr), bismuth (Bi), M, N, Q, X, Y and oxygen (O), relative to 1 atom of iron (Fe), and where
$0.2 \leq i \leq 100$;
$0 \leq j \leq 2$;
$j < i$;
$0 \leq k \leq 2$;
$k < i$;
$0.05 \leq m \leq 10$;
$m > j$;
$0 \leq n \leq 200$;
$0 \leq q \leq 8$;
$0 \leq x \leq 30$;
$0 \leq y \leq 8$; and
r is the number of oxygen atoms required to satisfy the valence requirements of the component elements other than oxygen present in formula (II), where
$4 \leq m+n+q+x+y \leq 200$;
$0 \leq q+x+y \leq 30$,
wherein the catalyst has a surface area of from 2 to 500 m²/g as determined by the Brunauer-Emmett-Teller (BET) method.

In an exemplary embodiment of the above described catalytic compositions, $0 \leq a \leq 3$; $0.04 \leq b \leq 20$; $0 \leq c \leq 15$; $0 \leq d \leq 175$; $0 \leq e \leq 5$; $0 \leq f \leq 2$; $3 \leq c+d+e+f \leq 175$; and $0 \leq e+f \leq 5$ for formula (I); and $0.3 \leq i \leq 50$; $0 \leq j \leq 1.5$; $j<i$; $0 \leq k \leq 1.5$; $k<i$; $0.1 \leq m \leq 8$; $m>j$; $0 \leq n \leq 100$; $0 \leq q \leq 3$; $0 \leq x \leq 10$; $0 \leq y \leq 3$; $4.5 \leq m+n+q+x+y \leq 100$; and $0 \leq q+x+y \leq 10$ for formula (II).

In another exemplary embodiment of the above described catalytic compositions, $0 \leq a \leq 1$; $0.05 \leq b \leq 15$; $0.1 \leq c \leq 9$; $0 \leq d \leq 150$; $0 \leq e \leq 2$; $0 \leq f \leq 1$; $5 \leq c+d+e+f \leq 150$; and $0 \leq e+f \leq 2$ for formula (I); and $0.5 \leq i \leq 50$; $0 \leq j \leq 0.5$; $j<i$; $0 \leq k \leq 0.75$; $k<i$; $0.2 \leq m \leq 5$; $m>j$; $0 \leq n \leq 60$; $0 \leq q \leq 1.5$; $0 \leq x \leq 5$; $0 \leq y \leq 2$; $5 \leq m+n+q+x+y \leq 60$; and $0 \leq q+x+y \leq 7.5$ for formula (II).

In an exemplary embodiment, the catalyst composition comprises a mixture of the mixed oxide catalysts of formula (I) and formula (II).

In an exemplary embodiment, the catalyst composition consists of a mixture of the mixed oxide catalysts of formula (I) and formula (II).

In an exemplary embodiment, the catalyst composition comprises a mixed oxide catalyst of formula (I).

In an exemplary embodiment, the catalyst composition comprises a mixed oxide catalyst of formula (II).

In an exemplary embodiment, the catalyst composition consists of a mixed oxide catalyst of formula (I).

In an exemplary embodiment, the catalyst composition consists of a mixed oxide catalyst of formula (II).

In an exemplary embodiment, the catalyst composition of the present invention can be used in either unsupported (bulk) or supported form. Suitable supports (also referred to herein as "carriers") include, but are not limited to, silica, zirconia, titania, alumina and mixtures thereof. The support may comprise from 0% up to 99%, such as 10% up to 95%, such as 10% up to 90%, such as 20% up to 80%, such as 30% up to 80%, such as 40% up to 80%, such as 50% up to 80%, by weight of the catalyst composition.

In an exemplary embodiment, the support is colloidal silica having an average particle size ranging from approximately 2 to 1,000 nm, such as 2 to 900 nm, such as 10 to 700 nm, such as 10 to 500 nm, such as 10 to 300 nm, such as 10 to 200 nm, such as 10 to 100 nm, in diameter.

In an exemplary embodiment, the catalyst composition of the present invention can be shaped, with or without an organic or inorganic binder, into a suitable form that includes, for example, spheres, granules, pellets, extrudates, cylinders, trilobes, quadrilobes, ribs, rings, monoliths, wagon wheels, gauzes and mixtures thereof.

In various particular embodiments, the molar ratios of Mo/Fe vary from approximately 50 to 2 and give unexpected results as evidenced by high HCN yields and $CH_3OH$ conversions.

In one embodiment, the catalyst composition of the present invention is coated onto a cordierite monolith. The coating process parameters, slurry solids content, particle size, pH, viscosity, and other parameters can be adjusted or optimized as needed to achieve commercially durable adhesion and a uniform coating. The catalyst composition is coated onto a monolith structure to give low backpressure. The catalyst composition can also be loaded onto one or more desired form of carriers selected from, for example, spheres, granules, pellets, extrudates, cylinders, trilobes, quadrilobes, ribs, rings, monoliths, wagon wheels, gauzes and mixtures thereof. The monolith can be prepared from one or more materials selected from cordierite, ceramic, metallic, zeolite, carbides, mullite, alumina, clays or carbon and mixtures thereof. The monolith preferably comprises one or more materials selected from cordierite, ceramic, or metallic and mixtures thereof. The coating may be conducted in a single step or in multiple steps by, for example, dip coating, wash coating, curtain coating, vacuum coating, chemical vapor deposition or sputter coating or combinations thereof.

Another aspect of the invention is directed to a process for preparing a catalyst composition comprising or consisting of a mixed oxide catalyst represented by formula (I) as described herein, the process comprising:

(i) preparing a first mixture (mixture A) using source compounds of elements Cr and/or W in an aqueous solution; full or partial amounts of elements Bi, Sb, As, P, and/or a rare earth metal; full or partial amounts of elements Fe, Ru, and/or Os; an alkali metal element and/or an alkaline earth metal element; full or partial amounts of elements of Co, Rh, Ir, Ni, Pd, Pt, Cu, Ag, Au, Zn, Cd, Hg, Mn, Re, V, Nb, Ta, Se, Te, Hf, B, Ga, In, Tl, Ge, Sn, and/or Pb;

(ii) preparing a second mixture (mixture B) using source compounds of at least one or more of full or partial amounts of Mo, Si, Ti, Zr, and Al in an aqueous solution, and of remaining amounts of the step (i) elements to meet the above identified catalyst composition;

(iii) adding the mixture A to the mixture B to react and form a precipitate slurry, optionally using ammonia or other conventional base compounds to adjust pH;

(iv) filtering the precipitate slurry, and optionally mixing the precipitate with the source compounds of the remaining amounts of the step (ii) Mo, Si, Ti, Zr, and Al elements to meet the above-identified catalyst composition, to form a catalyst precursor; and (v) drying and calcining the catalyst precursor to form the catalyst composition.

A further aspect of the invention is directed to a process for preparing a catalyst composition comprising or consisting of a mixed oxide catalyst represented by formula (II) as described herein, the process comprising:

(i) preparing a first mixture (mixture A) using source compounds of the elements Fe, Cr and Bi in an aqueous solution; full or partial amounts of at least one or more of the elements Ce and/or Sb; full or partial amounts of the elements La, Pr, Nd, Pm, Sm, Eu, Gd, Tb, Dy, Ho, Er, Tm, Yb, Lu, Ti, Zr, Hf, B, Al, Ga, In, Tl, Si, Ge, Sn, Pb, P and/or As; full or partial amounts of the elements W, Ru and/or Os; full or partial amounts of the elements Co, Rh, Ir, Ni, Pd, Pt, Cu, Ag, Au, Zn, Cd, Hg, Mn, Re, V, Nb, Ta, Se and/or Te; and an alkali metal and/or an alkaline earth metal;

(ii) preparing a second mixture (mixture B) using source compounds of at least one or more of full or partial amounts of Mo, Si, Ti, Zr, and Al in an aqueous solution, and of remaining amounts of the step (i) elements to meet the above identified catalyst composition;

(iii) adding the mixture A to the mixture B to react and form a precipitate slurry, optionally using ammonia or other conventional base compounds to adjust pH;

(iv) filtering the precipitate slurry, and optionally mixing the precipitate with the source compounds of the remaining amounts of the step (ii) Mo, Si, Ti, Zr, and Al elements to meet the above-identified catalyst composition, to form a catalyst precursor; and (v) drying and calcining the catalyst precursor to form the catalyst composition.

In an exemplary embodiment of the process for preparing the catalyst compositions of the invention, the filtered precipitate slurry is mixed with the source compounds of any remaining amounts of the step (ii) Mo, Si, Ti, Zr and Al elements present in the mixed oxide catalysts of formula (I) and formula (II) to form the catalyst precursor.

In another exemplary embodiment of the process for preparing the catalyst compositions of the invention, the sum of the quantities of the elements added as "full or partial amounts" and as "remaining amounts" is equal to the total quantities of the individual elements present in the catalyst precursor and the final catalyst composition. The remaining amount is 0 to 100% of the full amount of the elements present in the final catalyst compositions.

In another exemplary embodiment of the process for preparing the catalyst compositions of the invention, any suitable source compounds containing more than one of the elements present in the mixed oxide catalysts of formula (I) and formula (II) can be used, where all the elements present in the source compounds are elements present in the final catalyst compositions.

The catalyst precursor is dried and calcined in air to form the final (i.e., finished) catalyst composition. Any conventional drying means can be used, including box drying, spray drying, belt drying, vacuum drying, hot plate evaporation, rotary evaporation etc. A preferred drying temperature is between 100° C. and 250° C., such as between 110° C. and 230° C. Any conventional calcination means can be used, including a box calciner, rotary calciner, belt calciner, etc. A preferred calcination temperature is between 300° C. and 900° C., such as between 450° C. and 700° C., such as between 450° C. and 550° C. The calcination may be conducted under various conditions, such as in the presence of air, an inert gas, carbon dioxide, steam or combinations thereof. In an exemplary embodiment, the calcining temperatures result in a phase transformation from a gamma morphology to an alpha or beta form. In a particular embodiment, the gamma form is more reactive than the alpha or beta forms.

The catalyst precursor (before drying and/or after drying), a partially calcined catalyst, and a fully calcined catalyst can be applied, loaded, and/or coated onto any other substrates and/or structured materials, and may also be shaped into a desired form. In one embodiment, the calcined catalyst is dip-coated onto a cordierite monolith to give low backpressure.

Another aspect of the invention is a process of treating alcohols (especially low carbon alcohols such as methanol, ethanol and propanol) or alcohol-containing mixtures, or nitriles or nitrile-containing mixtures, or ketones or ketone-containing mixtures, or aldehydes or aldehyde-containing mixtures, or carboxylic acids or carboxylic acid-containing mixtures, or esters or ester-containing mixtures, or ethers or ether-containing mixtures or mixtures of any of the foregoing in the presence of the catalyst compositions of the present invention under ammoxidation conditions to provide HCN and the corresponding nitriles.

Another aspect of the invention is a process of injecting one alcohol or a mixture of alcohols (such as $CH_3OH$, EtOH, propanol, butanol, allyl alcohol, phenylmethanol, diphenylmethanol, and triphenylmethanol), and/or nitriles (such as propionitrile (PN)) or nitrile-containing mixtures, and/or ketones (such as acetone) or ketone-containing mixtures, and/or aldehydes (such as formaldehdyde, acetaldehyde, acrolein) or aldehyde-containing mixtures, and/or carboxylic acids (such as acetic, formic and oxalic acids) or carboxylic acid-containing mixtures, and/or esters (such as methyl or dimethyl or methyl-ethyl ether esters of acetic, formic and oxalic acids) or ester-containing mixtures, or ethers (such as dimethyl ether, diethyl ether, and methyl ethyl ether) or ether-containing mixtures or mixtures of any of the foregoing in the presence of the catalyst compositions of the present invention under ammoxidation conditions to provide HCN and/or ACN or other corresponding nitriles. Other suitable compounds include, but are not limited to, acetals of formaldehdyde, acetaldehyde or acrolein, alkene nitriles, aromatic nitriles, polyols (such as ethylene glycol, propylene glycol or glycerol), trioxane (formaldehyde trimer) or mixtures of any of the foregoing.

In an exemplary embodiment of the invention, methanol is injected into a conventional AN production reactor effluent stream containing excess unconverted $NH_3$ and $O_2$ in the presence of the catalyst compositions of the present invention under ammoxidation conditions to produce HCN. FIG. 1 illustrates a suitable location for "the on-purpose HCN" production reactor (107) in a conventional AN production process or plant.

An exemplary embodiment of the invention involves the use of a dedicated secondary reactor containing a catalyst especially designed for the generation of additional HCN and nitriles or for destruction of excess $NH_3$. This arrangement of a secondary reactor in combination with a primary AN reactor is desirable because it yields significantly higher benefits compared to approaches for improving catalyst efficiency described in the conventional art. In a particular embodiment, the secondary reactor/catalyst design employs a catalyst composition of the present invention. In another embodiment, the catalyst may be any known ammoxidation catalyst, such as those referenced herein. FIG. 1 illustrates a specific embodiment showing a suitable location for the secondary reactor (107) in a conventional AN production process or plant.

In an exemplary embodiment of the invention, methanol is injected outside of an AN reactor into an AN reactor effluent stream containing unconverted ammonia ($NH_3$) and oxygen ($O_2$) with the intent to uncouple conventional co-production of HCN from AN reactors (propylene ammoxidation process) and HCN-production from $CH_3OH$ ammoxidation ($CH_3OH$ ammoxidation process), to produce HCN in the vapor phase under ammoxidation conditions in the presence of the catalyst compositions of the present invention and not limited to the excess $O_2$ limitations of a first AN reactor.

Another aspect of the invention is a process for converting unconverted $NH_3$ and $O_2$ present in the ammoxidation reactor effluent stream to HCN in the presence of the catalyst compositions of the present invention as a means for $NH_3$ removal that is superior to the conventional acidic neutralization of $NH_3$ required in a downstream operation in an AN and/or methacrylonitrile production process that is based on the ammoxidation of propylene, propane, isobutylene, isobutane or mixtures thereof.

Another aspect of the invention is a selective catalytic oxidation (SCO) process which oxidizes and eliminates unconverted and/or excess $NH_3$ present in an AN effluent gas stream by conversion of the $NH_3$ to $N_2$ by reaction with excess $O_2$ already present in the AN reactor effluent stream, which is superior compared to conventional $NH_3$ removal by acidic neutralization of $NH_3$ in a downstream operation in an AN production process.

In an exemplary embodiment of the invention, methanol is injected into a conventional AN production reactor effluent stream containing excess unconverted $NH_3$, and/or unconverted $O_2$, and/or unconverted propylene and/or propane, and/or unconverted isobutylene and/or isobutane or mixtures of any of the foregoing from the first or preceding reactor in the presence of the catalyst compositions of the present invention and/or other suitable known ammoxidation catalysts to produce HCN, acrylonitrile and methacrylonitrile, respectively.

In an exemplary embodiment of the invention, one alcohol or a mixture of alcohols (such as $CH_3OH$ and/or EtOH), and/or nitriles (such as propionitrile (PN)), and/or ketones (such as acetone), or aldehydes or aldehyde-containing mixtures, or carboxylic acids or carboxylic acid-containing mixtures, or esters or ester-containing mixtures, or ethers or ethers-containing mixtures, their derivatives, or mixtures of any of the foregoing are injected into a reactor effluent stream containing excess unconverted $NH_3$, and/or unconverted $O_2$, and/or unconverted methane and/or methanol, ethane and/or ethylene and/or ethanol, propylene and/or propane, and/or unconverted isobutylene and/or isobutane or mixtures of any of the foregoing from the first or precedent reactor to produce HCN and/or ACN and/or acrylonitrile, and/or methacrylonitrile, and/or other corresponding nitriles in the presence of the catalyst compositions of the present invention and/or other suitable known ammoxidation catalysts. Methanol, formaldehyde and dimethyl ether all can be oxidized to formic acid, suggesting that the reaction products and/or reactions of these different functional groups (i.e., hydroxyl, carbonyl, and ether) are the same or very similar with respect to oxidation. Ethers and esters both contain an ether linkage and react similarly, as evidenced by the fact that dimethyl ether ($CH_3$—O—$CH_3$) and methyl methanoate (H—COO—$CH_3$) both can be catalytically converted to ethanol (EtOH). Similarly, alcohols and nitriles can react similarly to methanol ($CH_3OH$) and PN. In addition to $CH_3OH$, ethanol (EtOH), acetone and PN, other suitable feeds include, but are not limited to, propanol, butanol, allyl alcohol, phenylmethanol, diphenylmethanol, triphenylmethanol, acetals of formaldehdyde, acetaldehyde, acrolein (such as mono acetals and dimethyl acetals), ketones (such as methyl ethyl ketone, cetyl acetone, cyclohexanone, methyl isopropyl ketone, methyl isobutyl ketone and cyclopentanone), aldehydes and dialdehydes (such as formaldehyde, acetaldehyde, propionaldehyde, butyraldehyde, benzaldehyde, tolualdehyde, furfural, and glyoxal and butanedial), saturated carboxylic acids and unsaturated carboxylic acids (such as carbonic acid, formic acid, acetic acid, propionic acid, butyric acid, valeric acid and hexanoic acid as exemplary of straight-chain, saturated carboxylic acids; and benzoic acid as exemplary of aromatic carboxylic acids; and oxalic acid and adipic acid as representative of dicarboxylic acids), linear and nonlinear esters (such as dimethyl esters and methyl-ethyl ether esters, and methyl, ethyl, propyl, butyl, and pentyl methanoates, ethanoates, propanoates, butanoates, pentanoates, hexanoates, benzoates and lactates), symmetrical and unsymmetrical ethers (such as dimethyl ether and diethyl ether, diisopropyl ether, methyl ethyl ether, methyl tert-butyl ether (MTBE), tert-amyl methyl ether, methyl sec-butyl ether, methyl phenyl ether, tetrahydrofuran, dioxane, dicyclopentyl ether, methyl phenyl ether, hydroxymethylfurfural ethers), alkane nitriles other than PN, alkene nitriles, aromatic nitriles, polyols (such as methanol polymers, ethylene glycol, propylene glycols or glycerol), trioxane (formaldehyde trimer), their derivatives or mixtures of any of the foregoing.

Another aspect of the invention is a process for the ammoxidation of an alcohol or alcohol-containing mixture, a nitrile or nitrile-containing mixture, a ketone or ketone-containing mixture, an aldehyde or aldehyde-containing containing mixture, a carboxylic acid or carboxylic acid-containing mixture, an ester or ester-containing mixture, an ether or ether-containing mixture, their derivatives or mixtures thereof comprising reacting the alcohol or alcohol-containing mixture, the nitrile or nitrile-containing mixture, the ketone or ketone-containing mixture, the aldehyde or aldehyde-containing containing mixture, the acid or acid-containing mixture, the ester or ester-containing mixture, the ether or ether-containing mixture, their derivatives or mixtures thereof with $NH_3$ and $O_2$ in the presence of a catalyst composition to provide HCN and/or ACN and/or the corresponding nitriles, wherein the catalyst composition comprises or consists of a mixed oxide catalyst of formula (I) or (II) or a mixture thereof.

In an exemplary embodiment of the process for ammoxidation, the alcohol is selected from the group consisting of $C_1$-$C_{10}$ alcohols (such as $C_1$-$C_8$ alcohols, such as $C_1$-$C_6$ alcohols, such as $C_1$-$C_4$ alcohols), allyl alcohol, phenylmethanol, diphenylmethanol, and triphenylmethanol.

In an exemplary embodiment of the process for ammoxidation, the alcohol is selected from the group consisting of $CH_3OH$, EtOH, propanol, butanol, polyols (such as ethylene glycol, propylene glycol and glycerol) and mixtures thereof.

In an exemplary embodiment of the process for ammoxidation, the nitrile is selected from the group consisting of alkane nitriles, alkene nitriles, aromatic nitriles and mixtures thereof.

In an exemplary embodiment of the process for ammoxidation, the nitrile is selected from the group consisting of acrylonitrile, acetonitrile, methacrylonitrile, propionitrile, butanenitrile, benzonitrile and mixtures thereof.

In an exemplary embodiment of the process for ammoxidation, the ketone is selected from the group consisting of saturated ketones, diketones, unsaturated ketones, cyclic ketones having the formula $(CH_2)_nCO$, where n=2, 3, 4, 5, 6, 7, 8, 9, 10, 11, 12 and 13, and mixtures thereof.

In a particular embodiment of the process for ammoxidation, the ketone is selected from the group consisting of acetone, methyl ethyl ketone, acetyl acetone, cyclohexanone, methyl isopropyl ketone, methyl isobutyl ketone, and cyclopentanone and mixtures thereof.

In an exemplary embodiment of the process for ammoxidation, the aldehyde is selected from the group consisting of formaldehyde, acetaldehyde, propionaldehyde, butyraldehyde, benzaldehyde, tolualdehyde, furfural, and glyoxal and butanedial and mixtures thereof; the carboxylic acid is selected from the group consisting of carbonic acid, formic acid, acetic acid, propionic acid, butyric acid, valeric acid, hexanoic acid, benzoic acid, oxalic acid, and adipic acid and mixtures thereof; the ester is selected from the group consisting of dimethyl esters and methyl-ethyl ether esters, and methyl, ethyl, propyl, butyl, and pentyl methanoates, ethanoates, propanoates, butanoates, pentanoates, hexanoates, and benzoates and mixtures thereof; and the ether is selected from the group consisting of dimethyl ether, diethyl ether, diisopropyl ether, methyl ethyl ether, methyl tert-butyl ether (MTBE), tert-amyl methyl ether, methyl sec-butyl ether, methyl phenyl ether, tetrahydrofuran, dioxane, dicyclopentyl ether, methyl phenyl ether, and hydroxymethylfurfural ethers and mixtures thereof.

In an exemplary embodiment of the process for ammoxidation, the source of the $O_2$ is air or excess unconverted $O_2$ from a reactor effluent and the source of the $NH_3$ is $NH_3$ independently provided via a feed line or is excess unconverted $NH_3$ from a reactor effluent.

In an exemplary embodiment of the process for ammoxidation, the reactor effluent is from an ammoxidation process, an oxidation process or a reduction process.

In an exemplary embodiment of the process for ammoxidation, the ammoxidation process is selected from propylene ammoxidation, isobutylene ammoxidation, propane or isobutane ammoxidation, alcohol (such as $CH_3OH$ or EtOH or propanol) ammoxidation and combinations thereof.

In an exemplary embodiment of the process for ammoxidation, the ammoxidation is of a nitrile (such as propionitrile (PN), acetonitrile or methacrylonitrile) or mixtures thereof.

In an exemplary embodiment of the process for ammoxidation, the ammoxidation is of acetone; methyl ethyl ketone; methyl esters of acetic, formic and propionic acid; dimethyl esters of oxalic acid; acetals of formaldehyde and acetaldehyde; acrolein; methyl, ethyl, and propyl ethanoates; dimethyl ether, diethyl ether, methyl ethyl ether, MTBE; or mixtures thereof.

In an exemplary embodiment of the process for ammoxidation, the $NH_3$ and $O_2$ are present in an AN effluent stream from a primary AN or ammoxidation reactor, and the alcohol or alcohol-containing mixture, the nitrile or nitrile-containing mixture, the ketone or ketone-containing mixture, the aldehyde or aldehyde-containing containing mixture, the carboxylic acid or carboxylic acid-containing mixture, the ester or ester-containing mixture, the ether or ether-containing mixture or mixtures thereof is reacted with the $NH_3$ and $O_2$ in the presence of a catalyst composition in the secondary reactor downstream of and connected directly or indirectly to the primary AN reactor outside of the AN or ammoxidation reactor.

In an exemplary embodiment of the process for ammoxidation, the catalyst composition comprises the mixed oxide catalyst of formula (I).

In an exemplary embodiment of the process for ammoxidation, the catalyst composition consists of the mixed oxide catalyst of formula (I).

In an exemplary embodiment of the process for ammoxidation, the catalyst composition comprises the mixed oxide catalyst of formula (II).

In an exemplary embodiment of the process for ammoxidation, the catalyst composition consists of the mixed oxide catalyst of formula (II).

In an exemplary embodiment of the process for ammoxidation, the catalyst composition comprises the mixed oxide catalyst of formula (I) and the mixed oxide catalyst of formula (II).

In an exemplary embodiment of the process for ammoxidation, the catalyst composition consists of the mixed oxide catalyst of formula (I) and the mixed oxide catalyst of formula (II).

Another aspect of the invention is a process for the ammoxidation of an alcohol or alcohol-containing mixture, a nitrile or nitrile-containing mixture, a ketone or ketone-containing mixture, an aldehyde or an aldehyde-containing mixture, a carboxylic acid or a carboxylic acid-containing mixture, an ester or an ester-containing mixture, an ether or an ether-containing mixtures, their derivatives, or mixtures of any of the foregoing, comprising reacting the alcohol or the alcohol-containing mixture, the nitrile or the nitrile-containing mixture, the ketone or the ketone-containing mixture, the aldehyde or the aldehyde-containing mixture, the carboxylic acid or the carboxylic acid-containing mixture, the ester or the ester-containing mixture, the ether or the ether-containing mixture, their derivatives, or mixtures of any of the foregoing with unconverted $NH_3$ and/or $O_2$ and/or unconverted alkanes, alkenes, aromatics, alcohols, aldehydes, their derivatives, including nitriles, and/or mixtures of any of the foregoing from the first or preceding reactor to produce HCN, and/or ACN, and/or acrylonitrile, and/or methacrylonitrile and/or other corresponding nitriles in the presence of the catalyst compositions of the present invention and/or other suitable known ammoxidation catalysts outside of the first or preceding ammoxidation or AN reactor.

Another aspect of the invention is a process wherein the unconverted $NH_3$ and/or $O_2$ present in the effluent stream of the primary ammoxidation reactor reacts with (i) injected organic (such as hydrocarbon) compounds including alcohols or alcohol-containing mixtures, nitriles or nitrile-containing mixtures, ketones or ketone-containing mixtures, aldehydes or aldehyde-containing mixtures, carboxylic acids or carboxylic acid-containing mixtures, esters or ester-containing mixtures, ethers or ether-containing mixtures, their derivatives, or mixtures thereof and/or (ii) additional components of unconverted alkanes, alkenes, aromatics, alcohols, aldehydes, their derivatives (including nitriles) and/or mixtures thereof present in the reactor effluent of the primary ammoxidation reactor or provided independently to produce additional HCN and nitrile products in the presence of the catalyst compositions of the present invention and/or other suitable ammoxidation catalysts in a secondary reactor downstream of and connected directly or indirectly to the primary AN reactor outside of the AN or ammoxidation reactor.

Another aspect of the invention is a process for the selective catalytic oxidation (SCO) of $NH_3$ to $N_2$ in the presence of $O_2$, comprising reacting the $NH_3$ with the $O_2$ (present in the air or from another source) in the presence of a SCO catalyst composition.

In an exemplary embodiment of the process for the selective catalytic oxidation (SCO) of $NH_3$ to $N_2$ in the presence of $O_2$, the catalyst composition comprises the mixed oxide catalyst of formula (I).

In an exemplary embodiment of the process for the selective catalytic oxidation (SCO) of $NH_3$ to $N_2$ in the presence of $O_2$, the catalyst composition consists of the mixed oxide catalyst of formula (I).

In an exemplary embodiment of the process for the selective catalytic oxidation (SCO) of $NH_3$ to $N_2$ in the presence of $O_2$, the catalyst composition comprises the mixed oxide catalyst of formula (II).

In an exemplary embodiment of the process for the selective catalytic oxidation (SCO) of $NH_3$ to $N_2$ in the presence of $O_2$, the catalyst composition consists of the mixed oxide catalyst of formula (II).

In an exemplary embodiment of the process for the selective catalytic oxidation (SCO) of $NH_3$ to $N_2$ in the presence of $O_2$, the catalyst composition comprises the mixed oxide catalyst of formula (I) and the mixed oxide catalyst of formula (II).

In an exemplary embodiment of the process for the selective catalytic oxidation (SCO) of $NH_3$ to $N_2$ in the presence of $O_2$, the catalyst composition consists of the mixed oxide catalyst of formula (I) and the mixed oxide catalyst of formula (II).

In an exemplary embodiment, the $NH_3$ and $O_2$ are present in an effluent stream of a primary AN or ammoxidation reactor.

In an exemplary embodiment, the $NH_3$ and $O_2$ are reacted in the presence of the catalyst composition in a secondary reactor downstream of and connected directly or indirectly to the primary AN or ammoxidation reactor outside of the AN or ammoxidation reactor.

In an exemplary embodiment, the selection oxidation catalyst in the secondary reactor is a conventional selection oxidation catalyst.

In an exemplary embodiment of the process for oxidation in a secondary reactor, the secondary reactor is connected directly to the primary AN reactor.

In an exemplary embodiment of the process for oxidation in a secondary reactor, the secondary reactor is connected indirectly to the primary AN reactor.

In an exemplary embodiment, the secondary reactor comprises a fixed bed reactor where the catalyst is in a form selected from the group consisting of spheres, granules, pellets, extrudates, cylinders, trilobes, quadrilobes, ribs, rings, monoliths, wagon wheels, gauzes and mixtures thereof.

In an exemplary embodiment, the $NH_3$ is present in an $NH_3$ removal system or process and the $O_2$ or air is independently provided via a feed line or is already present with the $NH_3$.

In an exemplary embodiment, the $NH_3$ to be oxidized to $N_2$ and/or NOx for $NH_3$ removal is present in an exhaust stream wherein the exhaust gas stream contacts the catalyst of the present invention in the presence of $O_2$.

BRIEF DESCRIPTION OF THE DRAWINGS

The following figures illustrate particular embodiments of the present invention and are not intended to otherwise limit the scope of the present invention as described herein.

FIG. 1 illustrates a suitable location for "the on-purpose HCN" production reactor (107) in an otherwise conventional AN production plant.

DETAILED DESCRIPTION OF THE INVENTION

Definitions

Figure 2:
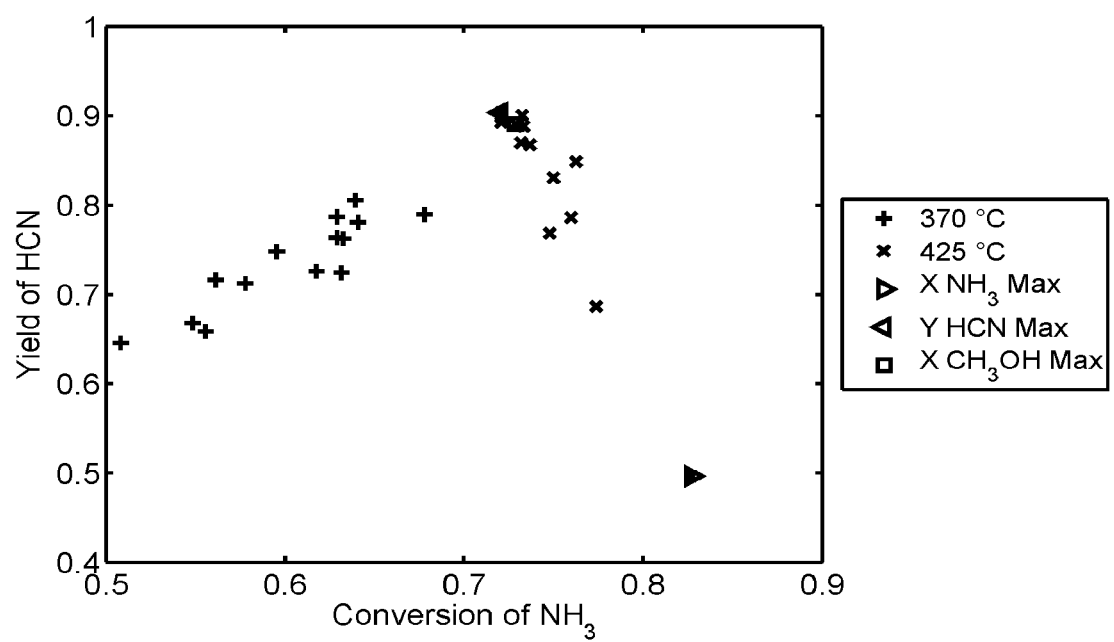
FIG. 2 illustrates a plot of test results indicating optimal catalyst formulations from test data. The figure also shows that the catalyst compositions appearing at the peak of the data are particularly effective in converting $NH_3$ to HCN in high yield.

As referred to herein, a "promoter" is one or more substances added to the catalyst composition, including a support, to increase the performance (i.e., activity, selectivity, yield, and stability) as evidenced by increased $CH_3OH$ and $NH_3$ conversions, HCN yield and/or other co-product yield(s), and reduced burning of the raw materials or products, including reduced burning of AN, and/or reduces yields of undesired by-products.

As referred to herein, "on-purpose HCN" is HCN intentionally produced to meet specific demand and/or made by using special feed supply or feed stock. More specifically, in this invention, "on-purpose HCN" refers to HCN prepared by using unconverted $NH_3$ and $O_2$ in an AN production reactor effluent stream by injecting $CH_3OH$ outside the main AN reactor.

As referred to herein, an "effluent stream" is a stream or flow exiting a chemical reactor. More specifically, in this invention, "effluent stream" refers to a hot stream existing in an AN production reactor and containing unconverted $NH_3$, $O_2$, AN product and optionally other by-products.

As referred to herein, "ammoxidation" is a process for the production of nitriles using ammonia and oxygen. In the process, the substrates that react with the $NH_3$ and $O_2$ are typically chemical compounds that include alkenes, alkanes, alcohols, aldehydes, ketones, esters, ethers and carboxylic acids. Typically, the compounds react with the $NH_3$ and $O_2$ in the vapor phase in the presence of a catalyst.

As referred to herein, an "ammoxidation catalyst" is a catalyst capable of enabling the ammoxidation of chemical compounds with $NH_3$ and $O_2$ to produce nitriles. The catalyst, which may include a variety of materials, such as metal oxides and zeolites, may also vary with the feed composition.

As referred to herein, a "coated monolith" is a monolith coated or applied with a thin layer of materials on the surface. The layer thickness varies with application and to-be-coated material and typically less than 300 microns. A thin layer of the catalysts of the present invention is coated onto a ceramic honeycomb monolith as an illustration in this invention.

As referred to herein, "AN reactor" and/or "AN production reactor" are reactors to manufacture or produce acrylonitrile (AN) as a target or key product. In a particular embodiment of the present invention, the reactor produces AN and/or by-product HCN from propylene, $NH_3$, and $O_2$ and operates at a temperature range of from 350° C. to 490° C.

As referred to herein, a "fluidized bed" is a catalytic reaction zone or bed where the particles of the catalyst composition and gas mixture are fluidized or behave like a fluid. In a particular embodiment of the present invention, the gas mixture passes through the particles of the catalyst composition (optionally in the form of microspheres) at sufficiently high velocities to suspend the particles and enable the bed to behave as a fluid. This fluidized feature typically causes effective mixing, heat and mass transfer so that it is widely used in the ammoxidation process which is an exothermic reaction (i.e., releases heat).

As referred to herein, a "fluidized bed reactor" is a type of reactor in which solids such as the catalyst compositions and/or reactant particles are fluidized. In general, the reactor contains features that promote extensive mixing, uniform temperature, and increased mass-transfer and reaction rates.

As referred to herein, "DOE" is "design of experiment"—i.e., a systematic method to determine the relationship between factors affecting a process and the output of that process. DOE is used to optimize catalyst design based on revealed cause-and-effect relationships which shows as a catalyst composition-and-performance correlation.

As referred to herein, "unexpected results" refers to unanticipated positive results, such as a higher or better HCN yield, $CH_3OH$ conversion, and/or HCN selectivity in an ammoxidation reaction compared to what is conventionally expected or normally obtained.

As referred to herein, the symbol "≤" includes the separate and distinct embodiments of "less than" (<) and "equal to" (=). Similarly, the symbol "≥" includes the separate and distinct embodiments of "greater than" (>) and "equal to" (=).

As referred to herein, a "rare earth metal" is well known to be an element from the lanthanide and actinide series of the periodic table and includes lanthanum, cerium, praseodymium, neodymium, promethium, samarium, europium, gadolinium, terbium, dysprosium, holmium, erbium, thulium, ytterbium, lutetium, actinium, thorium, protactinium, uranium, neptunium, plutonium, americium, curium, berkelium, californium, einsteinium, fermium, mendelevium, nobelium and lawrencium.

As referred to herein, an "alkali metal" is well known to be an element from Group 1 of the periodic table and includes lithium, sodium, potassium, rubidium, cesium and francium.

As referred to herein, an "alkaline earth metal" is well known to be an element from Group 2 of the periodic table and includes beryllium, magnesium, calcium, strontium, barium and radium.

As referred to herein, the concept of "valence" is well known and reflects the property of an element that determines the number of other atoms with which an atom of the element can combine.

As referred to herein, the "Brunauer-Emmett-Teller (BET) method" refers to the use the physical adsorption of gas molecules on a solid surface as a means for measuring the specific surface area of a material. Nitrogen is preferably used as an adsorbate. See, e.g., S. J. Gregg and K. S. W. Sing, "Adsorption Surface Area and Porosity," Academic Press, London, 1967.

As referred to herein, a $C_1$-$C_{10}$ alcohol includes, but is not limited to, methanol, ethanol, propanol, isopropanol, butanol, isobutanol, pentanol, isoamyl alcohol, hexanol, heptanol, 2-ethylhexanol, octanol, nonanol and decanol.

As referred to herein, "NOx" is a generic expression for various mono-nitrogen oxides, such as, for example, NO and $NO_2$.

All two-letter abbreviations of the elements of the periodic table used herein are well known (see, e.g., CRC Handbook of Chemistry and Physics, 95$^{th}$ edition, 2014 CRC Press).

FIG. 2 illustrates a plot of test results for identifying an optimal catalyst formulation from test data. In the plot, "X $NH_3$ Max" refers to "maximum $NH_3$ conversion", "Y HCN Max" refers to "maximum HCN yield", and "X $CH_3OH$ Max" refers to "maximum $CH_3OH$ conversion", respectively. The temperatures of 370° C. and 425° C. represent the reaction temperatures.

As described herein the present invention is directed to a catalyst composition comprising mixed oxides represented by the formula (I) or (II). In exemplary embodiments of formula (I), $0 \leq a \leq 3$; $0.04 \leq b \leq 20$; $0 \leq c \leq 15$; $0 \leq d \leq 175$; $0 \leq e \leq 5$; $0 \leq f \leq 2$; $3 \leq c+d+e+f \leq 175$; and $0 \leq e+f \leq 5$. In exemplary embodiments of formula (II), $0.3 \leq i \leq 50$; $0 \leq j \leq 1.5$; $j<i$; $0 \leq k \leq 1.5$; $k<l$; $0.1 \leq m \leq 8$; $m>j$; $0 \leq n \leq 100$; $0 \leq q \leq 3$; $0 \leq x \leq 10$; $0 \leq y \leq 3$; $4.5 \leq m+n+q+x+y \leq 100$; and $0 \leq q+x+y \leq 10$.

In other exemplary embodiments of formula (I), $0 \leq a \leq 1$; $0.05 \leq b \leq 15$; $0.1 \leq c \leq 9$; $0 \leq d \leq 150$; $0 \leq e \leq 2$; $0 \leq f \leq 1$; $5 \leq c+d+e+f \leq 150$; and $0 \leq e+f \leq 2$. In other exemplary embodiments of formula (II), $0.5 \leq i \leq 50$; $0 \leq j \leq 0.5$; $j<i$; $0 \leq k \leq 0.75$; $k<i$; $0.2 \leq m \leq 5$; $m>j$; $0 \leq n \leq 60$; $0 \leq q \leq 1.5$; $0 \leq x \leq 5$; $0 \leq y \leq 2$; $5 \leq m+n+q+x+y \leq 60$; and $0 \leq q+x+y \leq 7.5$.

In a particular embodiment, chromium (Cr) is used in a molar ratio of Cr/Fe=0.074. The amount of Cr in the catalyst composition can vary from zero to optimized non-zero levels. Elements in the same group in the periodic table exhibit similar physical or chemical characteristics of the outermost electron shells of their atoms as most chemical properties are dominated by the orbital location of the outermost electron. As the same VIB group elements with Cr and molybdenum (Mo), the tungsten (W) can be used as at various levels. The identified compositions are $0 \leq a \leq 5$ in formula (I) or $0 \leq j \leq 2$ and $j<i$ in formula (II).

In a particular embodiment, bismuth (Bi) is used at a molar ratio of Bi/Fe=0.13. The amount of Bi in the catalyst composition can vary from zero to optimized non-zero levels. Similarly, as the same VA group elements with Bi, the P, As, and Sb can be used at various levels. Sb is used in multiple embodiments to bring unexpected results which are related to its different oxidation states in the resultant catalyst materials in oxides or other forms, e.g., Sb(3+) in $Sb_2O_3$, Sb(4+) in $Sb_2O_4$, and Sb(5+) in $Sb_2O_5$. In multiple embodiments, the use of cerium results in unexpected results which are related to its reported oxygen storage feature and its different oxidation states in resulting catalyst materials in oxide form or other forms, e.g., Ce(4+) in $CeO_2$ and Ce(3+) in $Ce_2O_3$. Similarly to Ce, other rare earth elements in the same Lanthanide series can be used as at various levels. Exemplary identified compositions are $0.03 \leq b \leq 25$ in formula (I); or $0.2 \leq i \leq 100$; $0 \leq k \leq 2$; $k<i$; $0.05 \leq m \leq 10$; $m>j$; and $0 \leq n \leq 200$ in formula (II).

In a particular embodiment, iron (Fe) is used. The amount of Fe in the catalyst composition can vary from zero to optimized non-zero levels, or higher. The function of Fe can be related to its different oxidation states in the resultant catalyst materials in oxides or other forms, e.g., Fe (3+) in $Fe_2O_3$; Fe (3+/2+) in $Fe_3O_4$; and Fe (2+) in FeO. Similarly, as the same column elements of VIII group with Fe, Ru and Os can be used at various levels. For example, Ru is used in multiple embodiments at a molar ratio of Ru/Fe at 0 and 1.0. The identified compositions are $0 \le c \le 20$ in formula (I) or Fe=1 and $0 \le q \le 8$ in formula (II).

The catalyst compositions of the present invention can be used either unsupported (bulk) or supported form. Suitable supports include but not limited to silica, zirconia, titania, alumina, or mixtures thereof. The support may comprise as much as 90% in weight of the catalyst composition. The support may serve multiple roles, including as support to increase dispersion and reactants adsorption (i.e., $CH_3OH$ and/or $NH_3$), and/or as binder to improve physical strength and catalyst stability. Silica sol is a preferred supporting material. In multiple embodiments, silica sol is used at varying molar ratios of Si/Fe from 0 to 38.44. The silica sol with different particle size and sodium content can be used, but a silica sol is preferred to have an averaged particle size of 20 nm with a distribution range from 2 nm to 100 nm and sodium content less than 1000 ppm, much preferred less than 600 ppm, and even much preferred less than 200 ppm. In one embodiment, silica powder with a surface area of 730 $m^2/g$ is used and the resultant catalyst showed unexpected results and a BET surface area of 359.8 $m^2/g$.

In another embodiment, an unsupported catalyst composition showed unexpected results even when the BET surface area was 9.3 $m^2/g$. Therefore, the catalyst compositions of the present invention can be shaped, with and without an organic or inorganic binder, into an active unsupported catalyst in a suitable form.

In a particular embodiment, titanium dioxide ($TiO_2$) in a powder form is used to give unexpected results at molar ratios of Ti/Fe at 0 and 14.64. In a particular embodiment, Ce-modified zirconium (Zr) oxide and/or hydroxide powder and silica sol are used together at molar ratios of Zr/Fe=3.11 and Si/Fe=14.95 and give unexpected results. Alumina is used as a binder (embodiment not included) and the resultant catalyst also give unexpected results. Similarly, the element of Hf in the same IVB group with Ti and Zr, the elements of B, Ga, In, and Tl in the same IIIA group with Al, and the elements of Ge, Sn, Pb in the same IVA group with Si can be used as at various levels and forms. The identified compositions are $0 \le d \le 200$ in formula I or $0 \le n \le 200$ in formula (II). A variety of suitable supports or modified supports, including silica, in various forms or shapes can be used, including slurry, sol, gel, powder, bar, sheet, pellet and mixtures thereof.

In Ce- and/or Sb-containing embodiments, the presence of Co, Ni, Zn, Mn, and/or Re yields unexpected results. These elements may contribute multiple roles, such as forming redox couples from different oxidation states, increasing reactant (i.e., $CH_3OH$ and $NH_3$) adsorption, promoting reactant (i.e., $CH_3OH$ and $NH_3$) utilization, enhancing ammoxidation reaction rates, stabilizing active sites, providing Lewis acids with mild oxidation capabilities and isoelectronic configurations similar to Fe. In the presence of Ce and/or Sb, embodiments with combined Co, Ni, Zn, Mn, and Re molar ratios of from 0 to 6.04 yield unexpected results. It was observed that in the Ce-free and/or Sb-free embodiments, the catalyst compositions did not yield unexpected results. Similarly, Rh, Ir, Pd, Pt, Cu, Ag, Au, Cd, Hg, V, Nb, Ta, Se and/or Te can be used as at various levels and in various forms. The identified compositions are $0 \le e \le 8$ in formula (I) or $0 \le x \le 30$ in formula (II).

In Ce- and/or Sb-containing embodiments, Mg yielded unexpected results at molar ratios of Mg/Fe at 0 and 1.17. The Mg element may increase binding and stability, decoke, and/or aid epitaxial lattice matching. In Ce- and/or Sb-free embodiments, the resulting catalyst compositions did not yield unexpected results when the molar ratio of Mg/Fe was 0 or 1.17. Similarly, any other alkaline earth metal, alkali metal and/or mixtures thereof can be used at various levels and in various forms. The identified compositions were $0 \le e \le 8$; $0 \le f \le 3$; $1 \le c+d+e+f \le 200$; $0 \le e+f \le 8$ in formula (I) or $0 \le y \le 8$; $4 \le m+n+q+x+y \le 200$; and $0 \le q+x+y \le 30$ in formula (II).

The BET surface area of the catalyst compositions of the present invention in various exemplary embodiments may vary from 9.0 $m^2/g$ in unsupported catalyst compositions to 360 $m^2/g$ supported on high surface area silica powder.

In various exemplary embodiments, the molar ratio of Mo/Fe was 48:1 and yielded unexpected results. In an exemplary embodiment, the molar ratio of Mo/Fe was reduced to 2.2:1 and yielded unexpected results. In another exemplary embodiment, the molar ratio of Mo/Fe was 2.8:1 and yielded unexpected results.

In an exemplary embodiment, the catalyst compositions of the present invention are coated onto a cordierite monolith. The coated monolith was observed to yield unexpected results. The coating process parameters, slurry solids content, particle size, pH, viscosity, and other parameters can be adjusted or optimized as needed to achieve commercially durable adhesion and uniform coating. In an exemplary embodiment, the catalyst composition was coated onto a monolith structure to give low backpressure. The catalyst compositions can also be loaded onto one or more desired carrier forms. In an exemplary embodiment, the monolith is made from one or more materials selected from cordierite, ceramic, metallic, zeolite, carbides, mullite, alumina, clays or carbon and mixtures thereof. The monolith is preferably made of from one or more materials selected from cordierite, ceramic, or metallic and mixtures thereof.

As referred to herein, "source compounds" are compounds which provide one or more of the metals present for the catalyst compositions of the present invention. As referred to herein, "full or partial amounts" refer to a full or partial desired quantity of those elements in the above-described process steps (i) and (ii) based on the requirements of the identified catalyst composition formula, suggesting those elements may be used in more than one step and added more than once. If partial amounts of these elements are added, suggesting there are remaining amounts of these elements to be added to meet required quantities of these elements in the final catalyst composition from above identified catalyst composition formula. As referred to herein, "remaining amounts of step (i) elements" refer to those elements used in process step (i) but their exact quantities are not included based on the above identified catalyst composition. As referred to herein, "remaining amounts of step (ii) elements" refer to those elements used in process step (ii) but their exact quantities are not included based on the above identified catalyst composition. Therefore, "remaining amounts of step (i) elements" and "remaining amounts of step (ii) elements" refer to those quantities of step (i) and step (ii) elements required in the final catalyst composition which is not present in the step (i) and step (ii), respectively. As referred to herein, "remaining amounts of step (i) elements" and "remaining amounts of step (ii) elements" must be provided and/or added into the process before the catalyst precursor is dried and calcined to form the final catalyst composition. Either "full or partial amounts" or "remaining amounts" can be zero but they cannot both be zero simultaneously for each individual element of those elements present in the identified catalyst composition formula. The sum of the quantities of those individual elements added as "full or partial amounts" and then added as "remaining amounts" is equal to the required total quantities of those individual elements present in the final catalyst composition.

The remaining amounts of the step (i) elements in the above step (ii) and the remaining amounts of the step (ii) Mo, Si, Ti, Zr, and Al elements in the above step (iv) can be zero simultaneously, suggesting that those elements are added in the full desired quantity as required by above identified catalyst composition formula. In an exemplary embodiment, the source compounds of the Fe, Cr, Co, Gd, Mg, Sb, Ru, and Bi elements are added at their full desired quantities in the mixture A. The source compounds of Mo and Si are added at their full desired quantities in the mixture B. Remaining amounts of the above source compounds were not used and/or needed to form the catalyst precursor which were dried and calcined to form the final catalyst composition.

The source compounds of some elements, especially those optional elements in steps (i) and (ii) may be added once at the full amount required in the final catalyst composition but in different preparation steps. In a particular embodiment, ammonium perrhenate, represented by the chemical formula $NH_4ReO_4$ as the source compound of Re, is added in the preparation of the mixture A at the full amount required in the final catalyst composition. In another particular embodiment, ammonium perrhenate as the source compound of Re, is added in the preparation of the mixture B at the full amount required in the final catalyst composition. The same amount of $NH_4ReO_4$ is added differently in these two embodiments, both of which were observed to yield unexpected results. The source compounds of Re can be added in a partial amount in the mixture A and further added at the remaining amount in the mixture B to meet the full amount present in the final catalyst composition. Thus, the remaining amount can be 0-100% of the full amount of those elements required in the final catalyst depending on what portion of the element has been previously supplied.

In an exemplary embodiment, ammonium heptamolybdate (AHM) as a source compound of Mo was first dissolved in water for preparation of the mixture B. In a particular embodiment, AHM was dissolved in water to form a final mixture B which did not contain supporting materials or any other elements. In an exemplary embodiment, AHM as the source compound of Mo and silica sol (40%) as the source compound of Si were added for preparation of the mixture B where the AHM was first dissolved in water and no precipitation occurred in the mixture B after both the AHM and silica sol were added. The order of the addition to the mixture B was not critical, but in a particular embodiment, it is preferable that the soluble source compounds or high solubility source compounds were dissolved in the aqueous solution before the low solubility source compounds were added. In an exemplary embodiment, AHM as the source compound of Mo was first dissolved in water for preparation of the mixture B, and then $TiO_2$ powder as the source compound of Ti was added to the mixture B which became a particulate slurry after the $TiO_2$ addition. In another embodiment, AHM as the source compound of Mo was first dissolved in water for preparation of the mixture B, and then $SiO_2$ powder as the source compound of Si was added to the mixture B which also became a particulate slurry after the $SiO_2$ addition. The order of the addition of the source compound of Mo was not observed to be critical in the catalyst preparation. The source compound of Mo may be added at any time during and after the mixture preparation, precipitation, and filtration, but must be added before the catalyst precursor is dried. In a particular embodiment, molybdenum trioxide was added and mixed with the wet precipitate to form the catalyst precursor. In another particular embodiment, molybdic acid was added and mixed with the wet precipitate to form the catalyst precursor.

The pH of the mixture B may vary from 3 to 11 depending upon the source compounds added and their respective concentrations, but a neutral or basic mixture B, especially at a pH above 7, is preferred. A high pH mixture B (i.e., at a pH>9 or higher) can be added with any conventional inorganic or organic acids, such as, but not limited to, nitric acid, sulfuric acid, hydrochloric acid, phosphoric acid, and/or citric acid, formic acid, acetic acid, lactic acid, succinic acid, glycolic acid, or mixtures thereof to lower the pH to about 7 to 9. Various conventional bases such as, but not limited to, ammonia, ammonium carbonate, ammonium bicarbonate, sodium carbonate, sodium bicarbonate, sodium hydroxide, potassium carbonate, potassium bicarbonate, potassium hydroxide, and organic bases such as, but not limited to, urea, amines and amine salts, or mixtures thereof can be added if needed to raise the pH to about 7 to 9 when the mixture B has a pH lower than 7.

In the process step (i), the source compounds of Fe, Cr, and Bi elements, and of optional one or more of Sb, Sn, alkali metal, and alkali earth metal elements, and of optional one or more of full or partial amounts of rare earth metal, Co, Rh, Ir, Ni, Pd, Pt, Cu, Ag, Au, Zn, Cd, Hg, Mn, Re, V, Nb, Ta, Se, Te, Hf, B, Ga, In, Tl, Ge, Pb, Ru, Os, W, As, and P elements, were combined in an aqueous solution to form the mixture A. The resultant mixture A can be a homogeneous or non-homogeneous mixture, including a solution, particulate slurry, suspension and colloid. A homogeneous mixture is preferred but the reaction(s) among the source compounds added may also form a non-homogeneous mixture depending upon the properties of each individual source compound added and the properties of the resultant mixture, such as acidity. An acidic mixture (i.e., a pH below 7, especially at a pH below 3) is preferred. A high pH mixture (i.e., a pH>8 or higher) can be treated with conventional inorganic or organic acids, such as, but not limited to, nitric acid, sulfuric acid, hydrochloric acid, phosphoric acid, and/or citric acid to lower the pH to about 3 or to about 2 or lower. In one embodiment, the source compounds of Fe, Cr, Co, Gd, Mg, Sb, and Ru in an aqueous solution, and the source compound of Bi dissolved in a nitric acid and water mixture are added at fully desired quantities to form the mixture A which is non-homogeneous.

After the completion of the preparation of the mixture B as described above and in process step (ii), the mixture A is added to the mixture B to react and form a slurry. If needed, a conventional base can be added to participate and/or assist the precipitation process. In one embodiment, the mixture A comprising the required elements added at their fully desired quantities is added to the mixture B comprising the required elements added at their fully desired quantities, immediately forming a precipitate upon contact. In a particular embodiment, aqueous ammonia was added to assist the precipitation process. The precipitate slurry pH can vary from 5 to 10, such as from 6 to 9, such as from 7 to 8. The temperature can vary from 4 to 150° C., such as from 10 to 90° C., such as from 20 to 70° C. Any conventional mixing mechanism, devices and/or setup can be used to sufficiently combine and/or mix the source compounds and precipitate slurry in the solvent in the mixtures preparation, precipitation, and filtration. A uniform mixture is desired and/or preferred to lead to a more uniform catalyst precursor and final catalyst composition.

In an exemplary embodiment, water is used as a solvent in the catalyst composition preparation but other solvents can also be used such as alcohols, organic acids, diluted mineral acids (such as nitric acid), and mixtures thereof. The aqueous and/or organic solvents are capable of dissolving at least one of the source compounds of these elements. In a particular embodiment, water was used as the solvent for preparing mixtures A and B. The amount of water used in preparing the mixtures A and B varied with the solubilities of the source compounds, but should be present in at least an adequate amount to partially dissolve a portion of the source compounds to form an agitated mixture. Different ratios of water to source compounds were used to dissolve the source compounds and the ratios may be further optimized to facilitate mixing.

The source compounds of the elements required for the catalyst compositions of the present invention may be derived from any suitable sources, including known inorganic and metallo-organic materials. For example, the source compound of Mo includes, but is not limited to, ammonium heptamolybdate (AHM), molybdic acid, molybdenum dioxide, molybdenum trioxide, molybdenum pentoxide, molybdenum acetate, and molybdenum chloride. AHM, molybdic acid and molybdenum trioxide are preferred Mo source compounds in the present invention. Phosphoric acid ($H_3PO_4$) is representative of a source compound of phosphorus (P). Ammonium phosphomolybdate, represented by the chemical formula $(NH_4)_3PMo_{12}O_{40}$, can provide Mo and P oxides upon calcination. Therefore, ammonium phosphomolybdate is a suitable source compound of Mo and P where both Mo and P are required in the final catalyst composition.

In exemplary embodiments, the source compounds of Fe, Cr, and Bi are their corresponding nitrates. Metal salts containing a nitrate ion are generally soluble in water, so they are preferred source compounds of those metal elements, especially if they are readily available. Ferric nitrate, chromium nitrate and bismuth nitrate are preferred Fe, Cr, and Bi source compounds, respectively. Other source compound of Fe, Cr, and Bi may include, but are not limited to, their hydroxides, oxides, chlorides, sulfates and acetates.

In exemplary embodiments, the source compounds of Sb and Sn are antimony trichloride ($SbCl_3$) and tin chloride pentahydrate chloride ($SnCl_4 \cdot 5H_2O$). $SbCl_3$ is soluble in an alcohol such as EtOH but is readily hydrolyzed and precipitates in water. $SnCl_4 \cdot 5H_2O$ is readily soluble in water. Other source compounds of Sb and Sn may include, but are not limited to, their oxides, chlorides (e.g., $SbCl_5$ and $SnCl_2$), acetates and sulfates.

In a particular embodiment, the source compound of Mg is magnesium nitrate. The source compounds of alkali metal and alkaline earth metal elements include, but are not limited to, their oxides, hydroxides and salts. The hydroxides, which are generally water soluble, easily decompose to oxides upon drying or calcination.

In a particular embodiment, the source compound of Ce is cerium nitrate hexahydrate. The source compounds of Ce include, but are not limited to, cerium nitrate, ceric ammonium nitrate, cerium oxide, cerium hydroxide, cerium chloride, cerium oxalate, cerium carbonate, cerium sulfate, cerium acetate, and ceria-doped material. In an exemplary embodiment, the source compound of Ce was ceria-doped zirconium hydroxide which simultaneously served as a source compound of Zr. The remaining rare earth metals may supplied from any suitable conventional source that can be incorporated into the catalyst composition. For example, the source compound of Gd is gadolinium nitrate hexahydrate in a particular embodiment. Both Ce and Zr in the ceria-doped zirconium hydroxide should be a part of the total amount of Ce and Zr required in the final catalyst composition. Similar to ammonium phosphomolybdate and ceria-doped zirconium hydroxide, any suitable conventional source compounds containing more than one element listed in the catalyst composition formula can be used and all the elements present in the source compounds should be a part of total amount of these elements required in the final catalyst composition.

Remaining elements may come from any suitable conventional source and can be incorporated into a catalyst composition. In exemplary embodiments, the elements cobalt, nickel, copper, zinc and manganese may be introduced using their nitrate and/or carbonate salts. The element ruthenium may be provided from ruthenium chloride ($RuCl_3$).

In a particular embodiment, none of Si, Ti, Zr, Al, or their mixtures is used as supports or binders in the preparation. As described previously, the catalyst compositions can be used in an unsupported (bulk) form or alternatively, in a supported form. Suitable supports include, but are not limited to, silica, zirconia, titania, alumina, or mixtures thereof. The support may comprise as much as 90% in weight of the catalyst composition, such as up to 85%, such as up to 80%, such as up to 75%, such as up to 70%, such as up to 65%, such as up to 60%, such as up to 50%. In multiple embodiments, silica sol as a support and/or binder is added in the mixture B preparation before the precipitation. As described in the above preparation steps (ii)-(iv), remaining amounts of Mo, Si, Ti, Zr, and Al elements can be mixed with the precipitate to form the catalyst precursor. The support may be added any time during and after the mixture preparation, precipitation, and filtration, but must be added before the catalyst precursor is being dried. Similarly, any organic and/or inorganic binders can be added at any time in the preparation process. The described preparation process provides the catalyst having unexpected results or performance. All these source compounds may be combined together via a one-pot synthesis route to improve the process efficiency as long as the final catalyst composition satisfies performance requirements.

The catalyst precursor was dried and calcined in air to form the final catalyst. Any known drying means can be used, including box drying, spray drying, belt drying, vacuum drying, hot plate evaporation, rotary evaporation, etc. In an exemplary embodiment, the drying temperature was between 100° C. and 250° C., such as between 110° C. and 230° C. Any known calcination means can be used, including a box calciner, rotary calciner, and belt calciner. In an exemplary embodiment, the calcination temperature is between 300° C. and 700° C., such as between 450° C. and 600° C.

The catalyst precursor before and/or after before being dried, the partially calcined catalyst, and the calcined catalyst composition can be loaded onto one or more desired forms of carriers selected from trilobes, quadrilobes, ribs, rings, monoliths, spheres, granules, pellets, extrudates, cylinder, wagon wheels, gauzes and mixtures thereof. In one embodiment, the calcined catalyst composition is dip-coated onto a cordierite monolith to give a low backpressure. The catalyst precursor and catalyst composition may be applied, loaded, and/or coated onto other substrates and/or structured materials, and may be shaped into a desired form.

The catalyst compositions of the invention are useful for catalytic ammoxidation and/or ammonia selective oxidation. In a particular embodiment, the catalyst composition was produced in a batch process where the source compounds for the various component elements are combined via one or more steps to form a catalyst precursor and eventually the final catalyst composition after calcination. A continued process and/or processes that use and/or combine batch process can also be employed to produce the catalyst compositions of the present invention.

The catalyst compositions of the present invention may be prepared by any conventional procedures or methods known to those skilled in the art, such as, for example, deposition, impregnation, sol-gel, mechanical milling and/or blending, hydrothermal, and/or combustion methods. The catalyst or catalyst precursor mixed compositions of the present invention may also be prepared by refluxing/boiling a mixture of catalyst precursor metal oxides, fine metal powders and/or metal precursor salts followed by recovery, drying and calcination.

The catalyst compositions of the present invention are useful in ammoxidation processes of alcohols or alcohol-containing mixtures, or nitriles or nitrile-containing mixtures, or ketones or ketone-containing mixtures, or alcohol and nitrile and ketones co-containing mixtures, to provide HCN and corresponding nitriles.

The catalyst compositions of the present invention are useful in ammoxidation processes of one alcohol or a mixture of alcohols, such as $CH_3OH$ and/or EtOH, and/or nitriles, such as propionitrile (PN), and/or ketones, such as acetone, to HCN and/or ACN and other corresponding nitriles.

The catalyst compositions of the present invention are useful in ammoxidation processes of injecting $CH_3OH$ outside of a conventional AN production reactor, into an AN reactor effluent stream containing unconverted $NH_3$ and $O_2$, to produce HCN in the vapor phase under ammoxidation conditions that include conventional conditions.

The catalyst compositions of the present invention are useful in ammoxidation processes of injecting $CH_3OH$ outside of an AN reactor, into the AN reactor effluent stream containing unconverted $NH_3$ and $O_2$, to uncouple the conventional co-production of HCN from AN reactors (propylene ammoxidation process) and HCN-production from $CH_3OH$ ammoxidation ($CH_3OH$ ammoxidation process) to produce HCN and thus not be limited to the excess $O_2$ limitations of the first AN ammoxidation reactor.

The catalyst compositions of the present invention are useful in ammoxidation processes which use and convert excess unconverted $NH_3$ and $O_2$ present in an AN reactor effluent stream to HCN as a more effective means for $NH_3$ removal than conventional $NH_3$ neutralization techniques that require acid treatment in the downstream operation of the AN production process.

The catalyst compositions of the present invention are useful in SCO processes which oxidize and eliminate unconverted and/or excess $NH_3$ to $N_2$ by reaction with excess $O_2$ already present in the AN reactor effluent stream, as a more effective means for $NH_3$ removal compared to conventional $NH_3$ neutralization techniques that require acid treatment in a downstream operation in the AN production process.

Conventional conditions for alcohol ammoxidation are also well known in the prior art as evidenced by U.S. Pat. No. 7,763,225, herein incorporated by reference in its entirety. The ammoxidation reaction conditions employed in the present invention are those disclosed in the art for the ammoxidation of $CH_3OH$, with typical temperature ranges of 200 to 600° C., with preferred ranges of from 250 to 550° C., and most preferred ranges of from 300 to 500° C. The molar ratio of $NH_3$ and $O_2$ to $CH_3OH$ or nitrile is approximately stoichiometric so that most of the reactants will be consumed in the reaction. Usually, the ratio of $NH_3$ to $CH_3OH$ or nitrile is 0.7:1 to 2:1, preferably 0.9:1 to 1.3:1. Use of excess $NH_3$ is not desirable because the unconverted $NH_3$ must be removed, recovered and recycled, or is wasted. Air is the preferred $O_2$ source because it is inexpensive. However, pure $O_2$ or $O_2$-enriched air may also be used. Although fluidized bed operations may be preferred in various embodiments, the operation process can occur in a fixed bed, an ebullating bed, or a moving bed type of operation.

The catalyst compositions of the present invention are useful in the preparation of HCN and/or nitriles from ammoxidation of alcohols, such as $CH_3OH$ and/or EtOH, and/or nitriles, and/or ketones and provide significantly higher $CH_3OH$ conversions and HCN yields than comparative catalysts, including $CH_3OH$ ammoxidation catalysts (i.e., HCN-production from $CH_3OH$) and propylene ammoxidation catalysts (i.e., conventional HCN co-production from an AN reactor). In an exemplary embodiment using the catalysts of the present invention, the $CH_3OH$ conversion increases with temperature, the HCN selectivity also unexpectedly increases with temperature between, for example 350° C. and 400° C., and the maximum yield of HCN is unexpectedly achieved at 425° C. In a particular embodiment, the catalysts of the present invention provide a linear conversion fraction of $CH_3OH$ in a direct 1:1 proportion of $NH_3$ converted and their usage at least 95% at a temperature of 425° C. In another embodiment, HCN and ACN are produced from EtOH ammoxidation, with an increase in both HCN and nitrile formation. In yet another embodiment, HCN is produced from propionitrile (PN) ammoxidation. In a further embodiment, HCN is produced from acetone ammoxidation.

The present invention is also directed to HCN production by $CH_3OH$ ammoxidation using unconverted $NH_3$ present in a process effluent, such as an ammoxidation reactor effluent. A feed composition comprising $CH_3OH$, $NH_3$, AN, and $O_2$ is used to simulate an ammoxidation reactor effluent in which the $NH_3$, $O_2$, and AN represent residual $NH_3$, residual and optionally added $O_2$, and product AN existing from the AN production reactor and the $CH_3OH$ is injected outside of the AN reactor. In various exemplary embodiments, the catalysts of the present invention provide unexpectedly high $CH_3OH$ conversions and HCN yields in the feed of the simulated AN reactor effluent. In one embodiment, the $CH_3OH$ conversion and HCN yield were found to be nearly unchanged before and after AN injection into the $CH_3OH$ ammoxidation feed comprising $CH_3OH$, $NH_3$ and $O_2$. AN burning under the tested conditions was found to be negligible in multiple embodiments. Notably, AN present in the feed was not significantly oxidized and/or changed in the ammoxidation process. In yet another embodiment, the catalyst of the present invention provided close to 100% HCN selectivity at a temperature between, for example, 325 to 450° C. in the AN-containing feed.

The reaction (4) below represents a chemical reaction for HCN synthesis in the present invention using $CH_3OH$ injection, with residual $NH_3$ and $O_2$ from an AN reactor effluent stream, which involves the same chemistry as conventional $CH_3OH$ ammoxidation to HCN as shown in reaction (3). However, the $NH_3$ and $O_2$ in reaction (4)

originate from unconverted or residual NH$_3$ from an AN reactor effluent. The O$_2$ in reaction (4) originates from the AN reactor effluent and can also be added separately or jointly with CH$_3$OH injection into the reactor effluent composition and under process conditions. The process for HCN production in the present invention is not limited to the excess O$_2$ limitations of the first AN ammoxidation reactor. Reaction (5) illustrates a conventional means of removing unconverted NH$_3$ in the conventional ammoxidation process.

Process of the present invention for converting unconverted NH$_3$ to HCN:

$$CH_3OH + NH_3 \text{ (unconverted)} + O_2 \text{ (unconverted)} \rightarrow HCN + 3H_2O \quad (4)$$

Conventional process for removing unconverted NH$_3$ as (NH$_4$)$_2$SO$_4$:

$$2NH_3 \text{ (unconverted)} + H_2SO_4 \rightarrow (NH_4)_2SO_4 \quad (5)$$

A commercial objective for the present invention is the production of additional HCN over what is normally prepared from AN production reactors by using a hot AN reactor effluent stream feed that is fed CH$_3$OH by injection to a second "on purpose HCN production" reactor. This protocol prevents the waste of NH$_3$, heat and O$_2$ components already contained in the hot reactive gas stream from the AN production reactor. This objective is accomplished without degrading the AN, ACN, and HCN products that are already present in the exit gas from the primary reactor. A significant benefit is realized from combining the product flows from two serially positioned reactors because it enables all the combined products from both reactors to be isolated together without additional separation and purification operations. This process also has the benefit of significantly reducing the amount of acid needed for neutralizing the excess or unconverted NH$_3$ or other alternative means for eliminating NH$_3$ from the effluent streams. The reduction in the formation of large amounts of highly contaminated ammonium sulfate waste product is also a significant added benefit of the present invention.

The catalyst compositions of the present invention enable the use of low NH$_3$ and O$_2$ gas levels, particularly those that exist in outlet streams from AN production reactors at high (e.g., 400 to 500° C.) temperatures, and in the presence of many contaminants and products produced in the effluent stream from the AN production reactors. In the conventional art, such gas stream contaminants and by-products are considered spent and are treated as waste. In various exemplary embodiments using simulated feed conditions, the unconverted NH$_3$ is converted to HCN and/or ACN by reaction with CH$_3$OH, EtOH or other alcohols. The new effluent stream from two serially positioned reactors (an existing AN reactor and an ammoxidation reactor outside of the AN reactor) contains an increased overall amount of HCN and/or ACN produced as a result of the catalytic process without additional separation and purification operations. The removal of the unconverted NH$_3$ also beneficially results in a significantly reduced amount of ammonium sulfate waste and sulfuric acid needed for neutralization. Thus, the catalysts of the present invention allow for a process that is environmentally and economically superior to conventional processes.

Due to the limitations inherent in conventional AN production catalysts and process performance, AN reactor effluent streams typically contain unconverted NH$_3$ and O$_2$. This residual NH$_3$ requires additional processing (i.e., separation/neutralization) to avoid rapid and unwanted polymerization and the formation of undesired side reactions and/or fouling solids in downstream equipment and/or measures to mitigate potentially detrimental environmental emissions. The removal of unconverted NH$_3$ also leads to a significant reduction in the sulfuric acid demand for neutralization of the ammonia as well as the ammonium sulfate waste that is generated as a result of the neutralization. The present invention now makes it possible to opportunistically convert this currently unused, wasted and potentially detrimental NH$_3$ (and O$_2$) into useful HCN products by reacting the "as is" feed gas product effluent originating from an AN production plant with alcohols such as CH$_3$OH using the novel catalyst compositions of the present invention as described herein, thereby boosting the overall yield of HCN.

Although AN and HCN production catalysts have existed commercially for years, the catalysts are generally unpredictable and complex, typically consisting of a mixture of micro-crystalline and nano-sized solids containing such disparate elements such as Sb, Bi, Fe, and Mo and requiring support adhesion chemistry to attach the catalyst to inert surface materials to ensure their proper functioning. In contrast, the catalysts of the present invention achieved high yields with short residence times of 0.001 to 50 seconds, and with selectivities of >90%, such as >95%, such as >97%, such as >99%, even under severe thermal and shear conditions. These observed performances are also possible under conventional engineering controls.

In an exemplary embodiment, an advanced packed bed reactor was utilized for on-purpose HCN production using a simulated feed as an AN reactor effluent to meet the dual constraints of pressure drop and heat transfer limits that are present in existing AN production plants.

In an exemplary embodiment, a structured packed bed using a monolith coated with the catalyst composition of the present invention to generate on-purpose HCN via CH$_3$OH ammoxidation while incurring a low pressure drop and minimal or no degradation of AN is one of the main features of the present invention. One advantage of this structured packed bed technology is the facile retrofitting of existing AN production plants based on conventional technologies to accommodate the benefits associated with the present invention, thereby significantly reducing the majority of the capital and operating costs otherwise required for a new standalone plant for commercial scale HCN production. In addition to honeycomb monolith, other structured materials and/or substrates can be used, such as, but not limited to, a catalytic foam comprising or consisting of metal, cordierite, ceramic, metallic, zeolite, carbides, mullite, alumina, clays, carbon or other materials.

The present invention reflects the result of the inventors' efforts to prepare "on-purpose" HCN at lower capital costs by making use of the available residual NH$_3$ generated in AN reactor effluent streams. This process is sufficiently versatile to be easily and rapidly integrated into other existing processes that generate waste and/or residual NH$_3$ and/or O$_2$ in effluent streams.

Ammonium sulfate represents a large volume waste product formed when sulfuric acid is used to scrub the NH$_3$ generated from an AN reactor effluent stream. Use of the sulfuric acid simultaneously acidifies the AN product to prevent its potentially catastrophic polymerization into process-fouling poly-AN (PAN) solids. The AN condensate is also observed to contain the co-product HCN and several organic by-products, subsequently sent to waste. The dilute and complex content of the AN production reactor hot effluent stream is associated with the conditions required to produce HCN through reaction with $CH_3OH$. While the source concentration is low, the $NH_3$ content represents a significant commercial quantity of HCN if the reaction time and back pressure of any contacting device used could be significantly reduced, and rendered effective at the low $NH_3$ and $O_2$ partial pressures/levels present in a typical AN reactor effluent stream. The requirement that the AN and HCN components of the stream not be degraded by the catalyst and reaction zone treatment is critical to the success of the present invention.

In addressing the failure of the conventional art to avoid the generation of sulfate wastes, the present invention significantly reduces the required quantity of ammonium sulfate waste by using the residual $NH_3$ instead as raw material for the production of a HCN co-product prior to acid neutralization of the AN production process.

The conventional art describes a $Zn^{2+}$ ion-based reversible $NH_3$ recovery technology in U.S. Pat. No. 6,838,069 which is incorporated by reference in its entirety. The technology of the present invention represents a means for pre-concentrating the $NH_3$ present in the effluent stream to render it more concentrated.

The present invention increases the yield of one or both of the main co-products (i.e., HCN and ACN) after the preparation of AN in an AN reactor while (1) saving on the raw material costs associated with the increase in co-product yields; and (2) achieving the same or superior conversion and selectivity to the desired co-products (on a carbon basis) as obtained with the use of alcohols such as $CH_3OH$, EtOH, and the like. In multiple embodiments, $CH_3OH$ ammoxidation chiefly yielded HCN while EtOH ammoxidation yielded both HCN and ACN in a simulated effluent feed containing AN. The relative amounts of HCN and ACN can be controlled by employing an alcohol mixture with varying ratios of $CH_3OH$ to EtOH. A desirable increase in the production of HCN and ACN during the production of AN can be achieved using crude alcohol mixtures.

A significant distinction between the present invention and the conventional art is the novel high performance catalyst compositions as described herein and a means for decoupling the primary reactor catalyst/process and its limitations from $NH_3$ conversion by using a separate series reactor in the effluent line. This arrangement enables the primary reactor to continue to employ conditions (e.g., $O_2$/hydrocarbon ratio, $NH_3/NH_3$ ratio, temperature, superficial velocity, etc.) that are catalyst optimized separately from the series reactor of this invention. As used herein, "hydrocarbon" refers to organic compounds naturally present in the effluent or added to the effluent that are generally capable of reacting in an ammoxidation reaction with the catalyst compositions of the present invention.

Another advantage of the present invention over the conventional art is the preparation of HCN in combination (i.e., with reactors linked serially) with main AN and HCN flow streams so as to eliminate the need to perform separate isolation and purification steps of this second source of HCN. In contrast, the conventional art performs AN production reactor modifications and does not employ a second reactor such as the one present in an embodiment of the invention. Also, in contrast to producing HCN by a stand-alone process (the Andrussow process or direct $CH_3OH$ to HCN reactor), the present invention significantly minimizes the additional capital required for dedicated backend end separation units (distillation columns, etc.) as it takes advantage of the existing AN backend separation units.

There are still further major differences between the present invention and the conventional art. Notably, the on-purpose HCN production of the present invention is performed outside of the primary AN reactor, but still preferably utilizes the highly reactive and hot effluent stream from a AN reactor as a feed to a separate "on purpose" HCN synthesis reactor. This unexpected capability achieved by the present invention is made possible by the highly active catalyst compositions of the present invention that also result in a highly selective $CH_3OH$ ammoxidation when contacted with the AN reactor effluent stream. It was also discovered that in an exemplary embodiment of the present invention a commercially significant high throughput rate can be achieved at substantially low total pressures by the novel use of structured catalytic packed beds, catalyst-coated tube(s) walls design or other high gas-to-solid surface area reactor designs, to accommodate high velocities, to enable high heat removal rates, and to achieve the required low pressure drop. The reactor design also has the benefit/advantage of being significantly compact compared to the packed bed designs and fluidized bed designs of the prior art.

The catalyst compositions of the present invention are useful in processes for the ammoxidation of the combined feed of $CH_3OH$, or other primary alcohols, or blends of alcohols, with an olefin or blends of olefins selected from propylene, isobutylene or mixtures thereof, to thereby form HCN, AN, methacrylonitrile and mixtures thereof, respectively.

In this invention, the on-purpose HCN production is applied to and occurs outside of the primary AN production reactor using the hot, chemically unstable (with respect to polymerization) crude AN gas stream containing residual excess raw materials (e.g., propylene, $NH_3$ and $O_2$), and by-products (e.g., $H_2O$, CO, and $CO_2$), and other co-products (e.g., $CH_3CN$ and the like), and a first HCN portion. This hot gas mixture exits fully from a first AN reactor and represents the feed gas to the (secondary) reactor of the present invention where a low molecular weight aliphatic alcohol, such as $CH_3OH$, is injected into the stream, typically immediately upstream of the catalyst composition of the present invention. In an exemplary embodiment, the simulated feed is preheated before entering the ammoxidation reactor.

The production of a second portion of HCN product, formed within the above-described gas stream is accomplished by the present invention through the combined use of a newly formulated, highly active, and uniquely selective, $CH_3OH$ ammoxidation catalyst, combined with a novel use of a structured bed reactor. This design provides a compact configuration utilizing high velocities at a low pressure drop enabling non-degradative, high speed and efficient mass contact to promote the selective HCN formation reaction. Despite the large gas flow rate involved, the reactor is compact compared to the regular packed and fluidized conventional bed designs.

In an exemplary embodiment, the on-purpose HCN production is performed outside of the primary AN synthesis reactor through the use of a secondary fluidized bed or fixed bed reactor containing a highly active and selective $CH_3OH$ ammoxidation catalyst and preferably using a structured fixed bed reactor (catalyst bed(s) could be placed inside the heat transfer tubes, outside or coated on the heat exchanger tube surface) to achieve required heat removal and minimize pressure drop. The preferred reactor will also be compact compared to the fluid bed designs of the prior art. This in-line processing provides a novel, adequate and desirable solution for converting unconverted $NH_3$ into value-added HCN.

In various exemplary embodiments, $NH_3$ is selectively oxidized to $N_2$ in the lack of $CH_3OH$ in the feed regardless of the presence or absence of AN in the simulated feed. The present invention may simply be used to oxidize and eliminate the excess $NH_3$ by reaction with excess $O_2$ already present in the AN reactor effluent stream. In this embodiment, no additional HCN or ACN is produced, but this approach leads to a significant reduction or complete elimination of the $NH_3$ neutralization required in the downstream quench in the AN production process. The present invention may also simply be incorporated or integrated into any $NH_3$ removal process to avoid conventional extraction, stripping or absorption means. In various exemplary embodiments, the catalyst compositions of the present invention allow for the selective catalytic oxidation (SCO) of $NH_3$, such as from the reactor effluent of a chemical process or a $NH_3$ removal system such as from mobile exhaust sources and/or stationary exhaust sources, to $N_2$ in the presence of $O_2$. The source of the $O_2$ may be from the air or independently provided via a feed line or already present with $NH_3$.

EXAMPLES

Catalyst Composition Preparation

In an exemplary embodiment, the source compounds of, for example, the elements Fe, Bi, Cr, Co, Sb, Gd, Mg, and Ru from compositional DOE are mixed in an aqueous solution to form mixture A. The source compounds of, for example, Mo and Si are mixed in an aqueous solution to form mixture B. The mixture A and the mixture B are combined, in the presence of ammonia, to form a precipitate slurry mixture. After filtration, the resultant precipitate is dried and calcined to form the catalyst composition. The formed catalyst composition can be further applied onto various conventional carriers via conventional means. Several preparation examples are provided for illustration purposes only.

Testing Conditions

In a particular embodiment, the $CH_3OH$ ammoxidation reactions are conducted in a ⅜" stainless steel fixed bed tubing reactor at atmospheric pressure. The catalyst is mixed with 0.5 g inert $\alpha\text{-}Al_2O_3$.

The $CH_3OH$ conversion ($X_{CH3OH}$) is calculated using the following formula:

$$X_{CH3OH}=(1-[CH3OH]_{OUT}/([CH3OH]_{OUT}+[CO]_{OUT}+[CO2]_{OUT}+[HCN]_{OUT}))*100\%$$

wherein $[CH_3OH]_{OUT}$, $[CO]_{OUT}$, $[CO_2]_{OUT}$ and $[HCN]_{OUT}$ are concentrations (vol. %) in the reactor effluent.

HCN selectivity ($S_{HCN}$) is calculated using the following formula:

$$S_{HCN}=([HCN]_{OUT}/([CO]_{OUT}+[CO2]_{OUT}+[HCN]_{OUT}))*100\%$$

HCN yield ($Y_{HCN}$) is calculated using the following formula:

$$Y_{HCN}=X_{CH3OH}*S_{HCN}$$

W/F (g·s)/(STP ml) is the contact time where W is weight of a catalyst; F is total inlet feed of gases in (STP ml)/s. For $CH_3OH$ ammoxidation, the catalyst is typically tested at 370° C., W/F=0.2 (g·s)/ml, and a feed composition of $NH_3$ (7 vol. %), $CH_3OH$ (6.9 vol. %), $O_2$ (13 vol. %) balanced with helium at W/F=0.20 (g·s)/ml for E1-E9, W/F=0.51 (g·s)/ml for CE1* and CE2*, W/F=0.025 (g·s)/ml for E10 and E11, 370° C. for E1-E6 and CE1-CE5, and 400° C. for E7-E11. E12 in Example 20 was tested with a feed composition of $NH_3$ (2.8 vol. %), $CH_3OH$ (1.49 vol. %), $O_2$ (4.97 vol. %), AN (2.18 vol. %) and balanced with helium at W/F=0.0083 (g·s)/ml and 400° C.

Catalyst Coated on a Monolith

Approximately 230 cells per square inch (cpsi) of cordierite monoliths are dip-coated with catalyst powder slurry. In a typical slurry preparation, approximately 1.2 kg of catalyst are added with 20 kg CeZr grinding media balls and 4.8 kg deionized water and ball-milled for 24 hours to get a slurry having a solids content about 20% by weight. If needed, various additives such as water and binders such as silica sol (e.g., Nalco 2327, 40% silica) can be added. The resultant slurry which had an average particle size of 0.3 microns and a pH of 1.5, was used to dip coat desired monolith coupons. Compressed air up to about 20 psi was used to blow out excess slurry from the channels. The coated monoliths were dried at 130-150° C. for up to 3 hours. The above dip-coating and drying steps were repeated several times to obtain a target catalyst loading of about 0.1-0.3 g/cc of monolith volume. The monoliths thus coated were calcined in air at 550° C. for 3 hours, with temperature ramp up and ramp down rates of 10° C./min. The slurry solids content, particle size, pH, viscosity, and other parameters were adjusted or optimized as needed to achieve commercially durable adhesion and uniform coating.

Comparative Example 1 (CE1, $Mn_{1.25}P_1Zn_{0.01}O_X$)

A $Mn_{1.25}P_1Zn_{0.01}O_x$ catalyst was prepared by a precipitation method according to U.S. Pat. No. 7,763,225 which discloses a $CH_3OH$ ammoxidation catalyst and process for HCN production. The catalyst was tested at 370° C. and W/F=0.51 (g·s)/ml. The feed composition was $NH_3$ (7 vol. %), $CH_3OH$ (6.9 vol. %), $O_2$ (13 vol. %) and balanced with helium. The results showed 12.4% $CH_3OH$ conversion and 11.6% HCN yield. The testing results are also shown in Table 1 and FIG. 3.

TABLE 1

Comparison of the catalysts of the present invention with comparative catalysts

| Example | Catalyst | W/F (g · s)/ml | X $CH_3OH$, % | Y HCN, % |
|---|---|---|---|---|
| CE1 | $Mn_{1.25}P_1Zn_{0.01}O_x$ | 0.51 | 12.4 | 11.6 |
| CE2 | Fe—Sb—U based mixed oxide | 0.20 | 32.1 | 31.4 |
|  |  | 0.51 | 36.1 | 33.9 |
| E1 | $FeMo_{47.97}Bi_{0.13}Cr_{0.07}Sb_{0.26}Gd_{2.0}Ru_{1.0}Co_{2.89}Mg_{1.17}O_x$ | 0.20 | 91.7 | 79.5 |
| E2 | $FeMo_{47.97}Bi_{0.13}Cr_{0.07}Sb_{0.26}Ce_{0.22}Gd_{2.0}Re_{0.26}Ru_{1.0}Ni_{2.89}Sn_{0.22}O_x$ | 0.20 | 89.3 | 76.4 |
| E3 | $FeMo_{47.97}Bi_{0.13}Cr_{0.07}Ce_{0.22}Re_{0.26}Ru_{1.0}Mn_{0.26}O_x$ | 0.20 | 87.0 | 73.2 |
| E4 | $FeMo_{47.97}Bi_{0.13}Cr_{0.07}Ce_{0.22}Co_{2.89}Mg_{1.17}Mn_{0.26}O_x$ | 0.20 | 83.5 | 75.0 |
| E5 | $FeMo_{47.97}Bi_{0.13}Cr_{0.07}Sb_{0.26}Re_{0.26}Ru_{1.0}Ni_{2.89}Zn_{2.89}Mg_{1.17}O_x$ | 0.20 | 77.1 | 67.4 |
| E6 | $FeMo_{47.97}Bi_{0.13}Cr_{0.07}Sb_{0.26}Gd_{2.0}Ni_{2.89}Mn_{0.26}Zn_{2.89}Sn_{0.22}O_x$ | 0.20 | 81.7 | 70.8 |
| CE3 | $FeMo_{47.97}Bi_{0.13}Cr_{0.07}Gd_{2.0}Re_{0.26}Ni_{2.89}Mn_{0.26}Cu_{2.89}Mg_{1.17}O_x$ | 0.20 | 51.4 | 7.1 |

TABLE 1-continued

Comparison of the catalysts of the present invention with comparative catalysts

| Example | Catalyst | W/F (g · s)/ml | X CH$_3$OH, % | Y HCN, % |
|---|---|---|---|---|
| CE4 | FeMo$_{47.97}$Bi$_{0.13}$Cr$_{0.07}$Gd$_{2.0}$Re$_{0.26}$Ni$_{2.89}$Co$_{2.89}$Zn$_{2.89}$O$_x$ | 0.20 | 27.9 | 23.8 |
| CE5 | FeMo$_{47.97}$Bi$_{0.13}$Cr$_{0.07}$Cu$_{2.89}$Zn$_{2.89}$Co$_{2.89}$Mn$_{0.26}$Mg$_{1.17}$O$_x$ | 0.20 | 50.8 | 31.8 |

Note:
X CH$_3$OH, % = CH$_3$OH conversion;
Y HCN, % = HCN yield.
E1-E6 represent catalysts of the present invention;
CE1-CE5 represent comparative catalysts;
CE1 is a comparative catalyst of CH$_3$OH oxidation to produce HCN.
All testing was conducted at 370° C. and W/F = 0.20 (g · s)/ml except for CE1 at 0.51(g · s)/ml and CE2 at W/F = 0.20 and 0.51 (g · s)/ml.

Comparative Example 2 (CE2, a Fe—Sb—U Based Mixed Oxide)

A Fe—Sb—U based mixed oxide catalyst was prepared by a precipitation method according to U.S. Pat. No. 7,763,225 which discloses a propylene ammoxidation catalyst. The catalyst was tested at 370° C., a feed composition of NH$_3$ (7 vol. %), CH$_3$OH (6.9 vol. %), O$_2$ (13 vol. %) and balanced with helium, and W/F=0.2 and 0.51 (g·s)/ml conditions, respectively. This catalyst showed lower HCN yield at W/F 0.20 (g·s)/ml than that at W/F=0.51 (g·s)/ml. Increasing W/F from 0.20 to 0.51 slightly increased the CH$_3$OH conversion and HCN yield. The results are also listed in Table 1 and FIG. 3 for comparison.

Example 1 (E1, FeMo$_{47.79}$Bi$_{0.13}$Cr$_{0.07}$Co$_{2.89}$Sb$_{0.26}$Gd$_{2.0}$Mg$_{1.17}$Ru$_{1.0}$Si$_{33.48}$O$_x$)

Mixture A was prepared by stirring 1250 ml of deionized water and then adding with 7.6 g of Fe(NO$_3$)$_3$·9H$_2$O, 0.56 g of Cr(NO$_3$)$_3$·9H$_2$O, 15.8 g of Co(NO$_3$)$_2$·6H$_2$O, 17 g of Gd(NO$_3$)$_3$·6H$_2$O, 5.64 g of Mg(NO$_3$)$_3$·6H$_2$O, 1.1 g of SbCl$_3$, 3.84 g of RuCl$_3$, and a mixture of 1.16 g of Bi(NO$_3$)$_3$·5H$_2$O and 20 ml of 50/50 mixture by volume of HNO$_3$ (70%) and deionized water. Mixture B was prepared by stirring 500 ml of deionized water and then adding with 159.334 g of ammonium heptamolybdate (AHM) and 94.6 g of silica sol (40 wt % silica). Mixture A and a 50/50 mixture of ammonia (28-30%) and deionized water were added to mixture B with a pH of 7.8-8.2 to form precipitate slurry of the catalyst precursor. The precipitate slurry was filtered and then dried at 120° C. overnight to get dry powder. The dry powder was transferred into an oven preheated at 300° C. for 1 hour and calcined at 550° C. for 3 hours with a heating rate of 10° C./min from 300° C. to 550° C. The resultant calcined powder was then directly used as catalyst for testing. The catalyst was tested at 370° C., W/F=0.2 (g·s)/ml, and a feed composition of NH$_3$ 7 (vol. %), CH$_3$OH (6.9 vol. %), O$_2$ (13 vol. %) and balanced with helium. The results showed 91.7% CH$_3$OH conversion and 86.7% HCN selectivity. HCN yield was 79.5%.

Example 2 (E2, FeMo$_{47.79}$Bi$_{0.13}$Cr$_{0.07}$Ni$_{2.89}$Sn$_{0.22}$Sb$_{0.26}$Gd$_{2.0}$Re$_{0.26}$Ce$_{0.22}$Ru$_{1.0}$Si$_{34.88}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 15.8 g of Ni(NO$_3$)$_3$·6H$_2$O, 17 g of Gd(NO$_3$)$_3$·6H$_2$O, 1.8 g of Ce(NO$_3$)$_3$·6H$_2$O, 1.45 g of SnCl$_4$·5H$_2$O, 1.12 g of SbCl$_3$, 3.84 g of RuCl$_3$, and a mixture of 1.16 g of Bi(NO$_3$)$_3$·5H$_2$O and 20 ml of 50/50 mixture of HNO$_3$ (70%) and deionized water. Mixture B was prepared similarly to Example 1 using 159.334 g of ammonium heptamolybdate (AHM), 2.12 g of NH$_4$ReO$_4$, and 98.6 g of silica sol (40 wt % silica). The subsequent steps of mixing, precipitation, filtering, drying and calcination are the same as Example 1. The catalyst was tested under the same conditions as in Example 1. The results showed 89.3% CH$_3$OH conversion and 85.6% HCN selectivity. HCN yield was 76.4%.

Example 3 (E3, FeMo$_{47.79}$Bi$_{0.13}$Cr$_{0.07}$Mn$_{0.26}$Re$_{0.26}$Ce$_{0.22}$Ru$_{1.0}$Si$_{24.36}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 1.8 g of Ce(NO$_3$)$_3$·6H$_2$O, 1.23 g of Mn(NO$_3$)$_2$·4H$_2$O, 2.12 g of NH$_4$ReO$_4$, 3.84 g of RuCl$_3$, and a mixture of 1.16 g of Bi(NO$_3$)$_3$·5H$_2$O and 20 ml of 50/50 mixture of HNO$_3$ (70%) and deionized water. Mixture B was prepared similarly to Example 1 using 159.33 g of ammonium heptamolybdate (AHM) and 68.84 g of silica sol (40 wt % silica). The subsequent steps of mixing, precipitation, filtering, drying and calcination were the same as in Example 1. The catalyst was tested under the same conditions as in Example 1. The results showed 87.0% CH$_3$OH conversion and 84.1% HCN selectivity. HCN yield was 73.2%.

Example 4 (E4, Mo$_{47.79}$FeBi$_{0.13}$Cr$_{0.07}$Ce$_{0.22}$Co$_{2.89}$Mg$_{1.17}$Mn$_{0.26}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 1.77 g of Ce(NO$_3$)$_3$·6H$_2$O, 15.46 g of Co(NO$_3$)$_2$·6H$_2$O, 5.49 g of Mg(NO$_3$)$_3$·6H$_2$O, 1.21 g of Mn(NO$_3$)$_2$·4H$_2$O, and a mixture of 1.16 g of Bi(NO$_3$)$_3$·5H$_2$O and 20 ml of 50/50 mixture of HNO$_3$ (70%) and deionized water. Mixture B was prepared similarly to Example 1 using 159.39 g of ammonium heptamolybdate (AHM) and 62.5 g of silica sol (40 wt % silica). The subsequent steps of mixing, precipitation, filtering, drying and calcination were the same as in Example 1. The catalyst was tested under the same conditions as in Example 1. The results showed 83.5% CH$_3$OH conversion and 89.8% HCN selectivity. HCN yield was 75.0%.

Example 5 (E5, Mo$_{47.79}$FeBi$_{0.13}$Cr$_{0.07}$Ni$_{2.89}$Zn$_{2.89}$Sb$_{0.26}$Mg$_{1.17}$Re$_{0.26}$Ru$_{1.0}$Si$_{32.42}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 15.8 g of Ni(NO$_3$)$_3$·6H$_2$O, 16.17 g of Zn(NO$_3$)$_2$·6H$_2$O, 5.64 g of Mg(NO$_3$)$_3$·6H$_2$O, 2.12 g of NH$_4$ReO$_4$, 3.84 g of RuCl$_3$, 1.11 g of SbCl$_3$, and a mixture of 1.16 g of Bi(NO$_3$)$_3$·5H$_2$O and 20 ml of 50/50 mixture of HNO$_3$ (70%) and deionized water. Mixture B was prepared by stirring 500 ml of deionized water and then adding with 159.33 g of ammonium heptamolybdate (AHM) and 91.6 g of silica sol (40 wt % silica). The subsequent steps of mixing, precipitation, filtering, drying and calcination were the same as in Example 1. The catalyst was tested under the same conditions as in Example 1. The results showed 77.1% CH$_3$OH conversion and 87.3% HCN selectivity. HCN yield was 67.4%.

Example 6 (E6, Mo$_{47.79}$FeBi$_{0.13}$Cr$_{0.07}$Ni$_{2.89}$Zn$_{2.89}$Mn$_{0.26}$Sn$_{0.22}$Sb$_{0.26}$Gd$_{2.0}$Si$_{31.36}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 15.8 g of Ni(NO$_3$)$_3$·6H$_2$O, 1.22 g of Mn(NO$_3$)$_2$·4H$_2$O, 17 g of Gd(NO$_3$)$_3$·6H$_2$O, 1.45 g of SnCl$_4$·5H$_2$O, 1.12 g of SbCl$_3$, and a mixture of 1.16 g of Bi(NO$_3$)$_3$·5H$_2$O and 20 ml of 50/50 mixture of HNO$_3$ (70%) and deionized water. Mixture B was prepared by stirring 500 ml of deionized water and then adding with 159.33 g of ammonium heptamolybdate (AHM) and 88.6 g of silica sol (40 wt % silica). The subsequent steps of mixing, precipitation, filtering, drying and calcination were the same as Example 1. The catalyst was tested under the same conditions as in Example 1. The results showed 81.7% CH$_3$OH conversion and 86.7% HCN selectivity. HCN yield was 70.8%.

Comparative Example 3 (CE3, FeMo$_{47.79}$Bi$_{0.13}$Cr$_{0.07}$Ni$_{2.89}$Cu$_{2.89}$Mn$_{0.26}$Gd$_{2.0}$Mg$_{1.17}$Re$_{0.26}$Si$_{35.75}$O$_x$)

Mixture A was prepared similarly to Example 1 using 1250 ml deionized water, 7.6 g of Fe(NO$_3$)$_3$·9H$_2$O, 0.56 g of Cr(NO$_3$)$_3$·9H$_2$O, 15.8 g of Ni(NO$_3$)$_3$·6H$_2$O, 12.64 g of Cu(NO$_3$)$_2$·6H$_2$O, 1.23 g of Mn(NO$_3$)$_2$·4H$_2$O, 5.64 g of Mg(NO$_3$)$_3$·6H$_2$O, 17 g of Gd(NO$_3$)$_3$·6H$_2$O, and a mixture of 1.16 g of Bi(NO$_3$)$_3$·5H$_2$O and 20 ml of 50/50 mixture of HNO$_3$ (70%) and deionized water. Mixture B was prepared similarly to Example 4 using 159.33 g of ammonium heptamolybdate (AHM), 2.12 g of NH$_4$ReO$_4$, and 101 g of silica sol (40 wt % silica). The subsequent steps of mixing, precipitation, drying and calcination were the same. The catalyst was tested under the same conditions as in Example 1. The results showed 51.4% CH$_3$OH conversion and 13.9% HCN selectivity. HCN yield was 7.1%.

Comparative Example 4 (CE4, Mo$_{47.79}$FeBi$_{0.13}$Cr$_{0.07}$Ni$_{2.89}$Zn$_{2.89}$Co$_{2.89}$Gd$_{2.0}$Re$_{0.26}$Si$_{38.44}$O$_x$)

Mixture A was prepared similarly to Example 1 using 1250 ml of deionized water, 7.6 g of Fe(NO$_3$)$_3$·9H$_2$O, 0.56 g of Cr(NO$_3$)$_3$·9H$_2$O, 15.8 g of Ni(NO$_3$)$_3$·6H$_2$O, 16.2 g of Zn(NO$_3$)$_2$·6H$_2$O, 15.8 g of Co(NO$_3$)$_2$·6H$_2$O, 17 g of Gd(NO$_3$)$_3$·6H$_2$O, and a mixture of 1.16 g of Bi(NO$_3$)$_3$·5H$_2$O and 20 ml of 50/50 mixture of HNO$_3$ (70%) and deionized water. Mixture B was prepared similarly to Example 4 using 159.33 g of ammonium heptamolybdate (AHM), 2.12 g of NH$_4$ReO$_4$, and 108.6 g of silica sol (40 wt % silica). The subsequent steps of mixing, precipitation, drying and calcination were the same. The catalyst was tested under the same conditions as in Example 1. The results showed 27.9% CH$_3$OH conversion and 85.3% HCN selectivity. HCN yield was 23.8%.

Comparative Example 5 (CE5, Mo$_{47.79}$FeBi$_{0.13}$Cr$_{0.07}$Cu$_{2.89}$Zn$_{2.89}$Co$_{2.89}$Mn$_{0.26}$Mg$_{1.17}$Si$_{32.67}$O$_x$)

Mixture A was prepared similarly to Example 1 using 1250 ml deionized water, 7.6 g of Fe(NO$_3$)$_3$·9H$_2$O, 0.56 g of Cr(NO$_3$)$_3$·9H$_2$O, 12.64 g of Cu(NO$_3$)$_2$·6H$_2$O, 1.22 g of Mn(NO$_3$)$_2$·4H$_2$O, 16.17 g of Zn(NO$_3$)$_2$·6H$_2$O, 5.644 g of Mg(NO$_3$)$_3$·6H$_2$O, 15.82 g of Co(NO$_3$)$_2$·6H$_2$O, and a mixture of 1.16 g of Bi(NO$_3$)$_3$·5H$_2$O and 20 ml of 50/50 mixture of HNO$_3$ (70%) and deionized water. Mixture B was prepared similarly to Example 1 using 159.33 g of ammonium heptamolybdate (AHM) and 92.3 g of silica sol (40 wt % silica). The subsequent steps of mixing, precipitation, drying and calcination were the same. The catalyst was tested under the same conditions as in Example 1. The results showed 50.8% CH$_3$OH conversion and 62.5% HCN selectivity. HCN yield was 31.8%.

Example 7 (E7, FeMo$_{47.79}$Bi$_{0.13}$Cr$_{0.07}$Ce$_{0.22}$Co$_{2.89}$Mg$_{1.17}$Mn$_{0.26}$Ti$_{14.64}$O$_x$)

Mixture A was prepared by stirring 1250 ml of deionized water and then adding with 7.6 g of Fe(NO$_3$)$_3$·9H$_2$O, 0.56 g of Cr(NO$_3$)$_3$·9H$_2$O, 1.77 g of Ce(NO$_3$)$_3$·6H$_2$O, 15.46 g of Co(NO$_3$)$_2$·6H$_2$O, 5.49 g of Mg(NO$_3$)$_3$·6H$_2$O, 1.21 g of Mn(NO$_3$)$_2$·4H$_2$O, and a mixture of 1.16 g of Bi(NO$_3$)$_3$·5H$_2$O and 20 ml of 50/50 mixture by volume of HNO$_3$ (70%) and deionized water. Mixture B was prepared by stirring 500 ml of deionized water and then adding with 159.39 g of ammonium heptamolybdate (AHM) and 25 g of titanium dioxide powder (TiO$_2$, approx. 88%). Mixture A and a 50/50 mixture of NH$_3$ (28-30%) and deionized water were added to mixture B with a pH of 7.8-8.2 to form precipitate slurry of the catalyst precursor. The precipitate slurry was filtered with washing assistance of using 1000 ml deionized water. The subsequent steps of drying and calcination were the same as Example 1. The catalyst was tested at 400° C. and other conditions are the same as those in Example 1. The results showed 97.6% CH$_3$OH conversion and 75.8% HCN yield, and are also listed in Table 2.

Example 8 (E8, FeMo$_{47.79}$Bi$_{0.13}$Cr$_{0.07}$Ce$_{0.22}$Co$_{2.89}$Mg$_{1.17}$Mn$_{0.26}$Si$_{22.12}$O$_x$)

Example 8 was prepared similarly to Example 7 but 25 g of SiO$_2$ powder (high surface area, BET SA=730 m$^2$/g) was used to substitute TiO$_2$ powder in preparing Mixture B. All other preparation conditions were the same as those in Example 7. The catalyst was tested at the same conditions as those in Example 7. The results showed 92.1% CH$_3$OH conversion and 74.6% HCN yield, and are also listed in Table 2.

TABLE 2

Testing results of various supports addition on $CH_3OH$ ammoxidation

| Example | Effluent product, % | | | | | | X $CH_3OH$, % | Y HCN, % |
|---|---|---|---|---|---|---|---|---|
| | $CO_2$ | $NH_3$ | $CH_3OH$ | $O_2$ | HCN | CO | | |
| E7 ($TiO_2$) | 0.95 | 3.12 | 0.13 | 6.49 | 4.16 | 0.25 | 97.6 | 75.8 |
| E8 ($SiO_2$) | 0.85 | 2.64 | 0.48 | 6.71 | 4.57 | 0.22 | 92.1 | 74.6 |
| E9 | 0.26 | 2.99 | 1.60 | 8.04 | 4.31 | 0.04 | 74.2 | 69.4 |

Note:
E9 has no support added.

Example 9 (E9, $FeMo_{47.79}Bi_{0.13}Cr_{0.07}Ce_{0.22}Co_{2.89}1$
$Mg_{1.17}Mn_{0.26}O_x$)

Example 9 was prepared similarly to Example 7 but the $TiO_2$ powder was not added. Mixture B was prepared by stirring 500 ml of deionized water and then adding with 159.39 g of ammonium heptamolybdate (AHM). Deionized water was not used in the filtration and all other preparation conditions were the same as those in Example 7. The catalyst was tested at the same conditions as those in Example 7. The results showed 74.2% $CH_3OH$ conversion and 69.4% HCN yield. Table 2 compared the results of Examples 7, 8, and 9.

Example 10 (E10,
$FeMo_{47.79}Bi_{0.13}Cr_{0.07}Sn_{1.12}Sb_{0.76}Si_{24.91}O_x$)

Figure 4A:
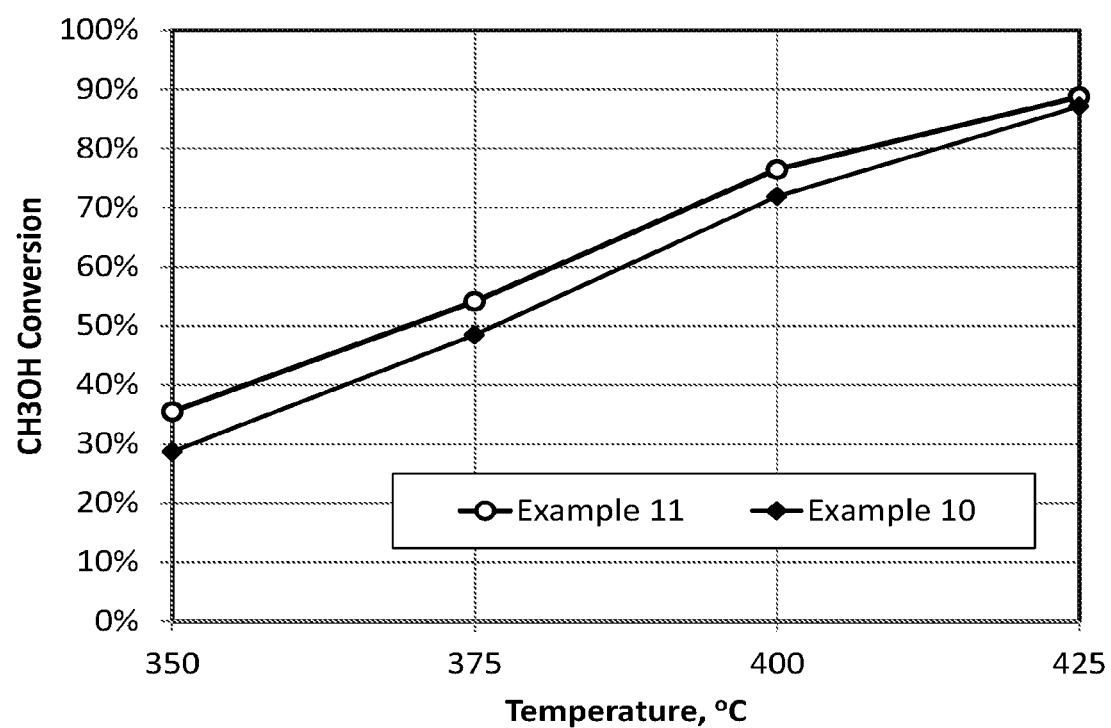
FIG. 4 illustrates the test results comparison of $CH_3OH$ conversion (FIG. 4A) and HCN yield (FIG. 4B) showing that a low Mo/Fe molar ratio (Mo/Fe=2.17 in Example 11) catalyst can exhibit a similar performance to that of a high Mo/Fe ratio (Mo/Fe=47.97 in Example 10) catalyst.
Figure 4B:
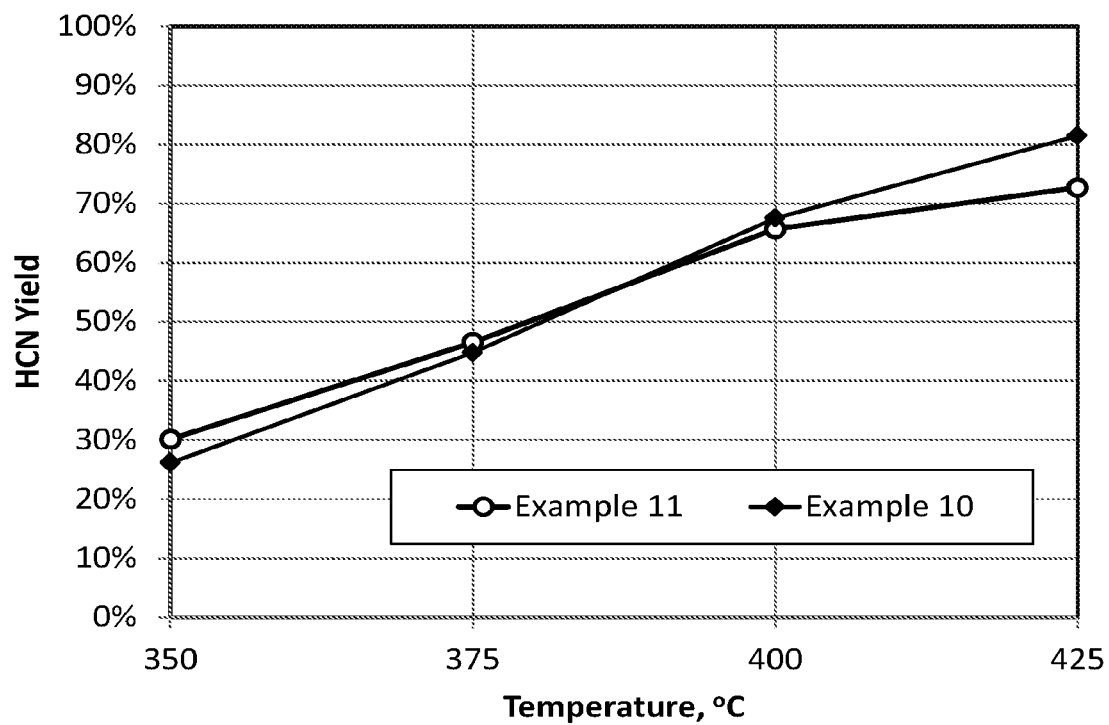

Mixture A was prepared similarly to Example 1 using 7.6 g of $Fe(NO_3)_3 \cdot 9H_2O$, 0.56 g of $Cr(NO_3)_3 \cdot 9H_2O$, 3.26 g of $SbCl_3$, 7.4 g of $SnCl_4 \cdot 5H_2O$, and 1.16 g of $Bi(NO_3)_3 \cdot 5H_2O$. Mixture B was prepared similarly to Example 1 using 159.334 g of ammonium heptamolybdate (AHM) and using 70.4 g of silica sol (40 wt % silica). The subsequent steps of mixing, precipitation, filtering, drying and calcination are the same as Example 1. The catalyst was tested W/F=0.025 (g·s)/ml and a feed composition of $NH_3$ (9.2 vol. %), $CH_3OH$ (8.0 vol. %), $O_2$ (12 vol. %) and balanced with helium at various temperatures. The results showed 71.9% $CH_3OH$ conversion and 67.5% HCN yield at 400° C. Additional results are shown in FIGS. 4A and 4B.

Example 11 (E11,
$FeMo_{2.17}Bi_{0.13}Cr_{0.07}Sb_{0.53}Sn_{0.48}Si_{22.65}O_x$)

Mixture A was prepared similarly to Example 1 using 3000 ml of deionized water and 76.0 g of $Fe(NO_3)_3 \cdot 9H_2O$, 5.60 g of $Cr(NO_3)_3 \cdot 9H_2O$, 29.0 g of $SnCl_4 \cdot 5H_2O$, 22.3 g of $SbCl_3$, and a mixture of 11.6 g of $Bi(NO_3)_3 \cdot 5H_2O$ and 100 ml of 50/50 mixture of $HNO_3$ (70%) and deionized water. Ammonium heptamolybdate (AHM) is not added to Mixture B. The Mixture B was prepared by stirring 4000 ml of deionized water and then adding with 640 g of silica sol (40 wt % silica). After the mixing and precipitation, the precipitate slurry was filtered to get a total of 1950.4 g of wet precipitate. Approximately 79.52 g of the wet precipitate was added with 2.766 g of molybdenum trioxide and mixed for 1 hour. The subsequent steps of drying and calcination were the same as Example 10. The catalyst was tested under the same conditions as those in Example 10. The results showed 76.4% $CH_3OH$ conversion and 65.7% HCN yield at 400° C. Additional results are shown in FIGS. 4A and 4B.

Example 12 (E12,
$FeMo_{2.81}Bi_{0.13}Cr_{0.07}Sb_{0.76}Sn_{1.12}Ce_{0.76}Zr_{3.11}Si_{14.95}O_x$)

Mixture A was prepared using 200 ml of deionized water and 7.64 g of $Fe(NO_3)_3 \cdot 9H_2O$, 0.56 g of $Cr(NO_3)_3 \cdot 9H_2O$, 7.4 g of $SnCl_4 \cdot 5H_2O$, 3.27 g of $SbCl_3$, and a mixture of 1.16 g of $Bi(NO_3)_3 \cdot 5H_2O$ and 10 ml of 50/50 mixture of $HNO_3$ (70%) and deionized water. Mixture B was prepared using 400 ml of deionized water, 11.3 g of ceria doped zirconium hydroxide (25.5% $CeO_2$) and 42.25 g of silica sol (40 wt % silica). After the mixing and precipitation, the precipitate slurry was filtered to get a total of 102 g of wet precipitate. Approximately 54.59 g of the wet precipitate was added with 4.71 g of molybdic acid and mixed for 1 hour. The subsequent steps of drying and calcination were the same as in Example 1. The catalyst was tested at the conditions listed in Examples 19, 20, and 21.

Example 13 (Temperature Optimization Study of E1 Catalyst)

Figure 5:
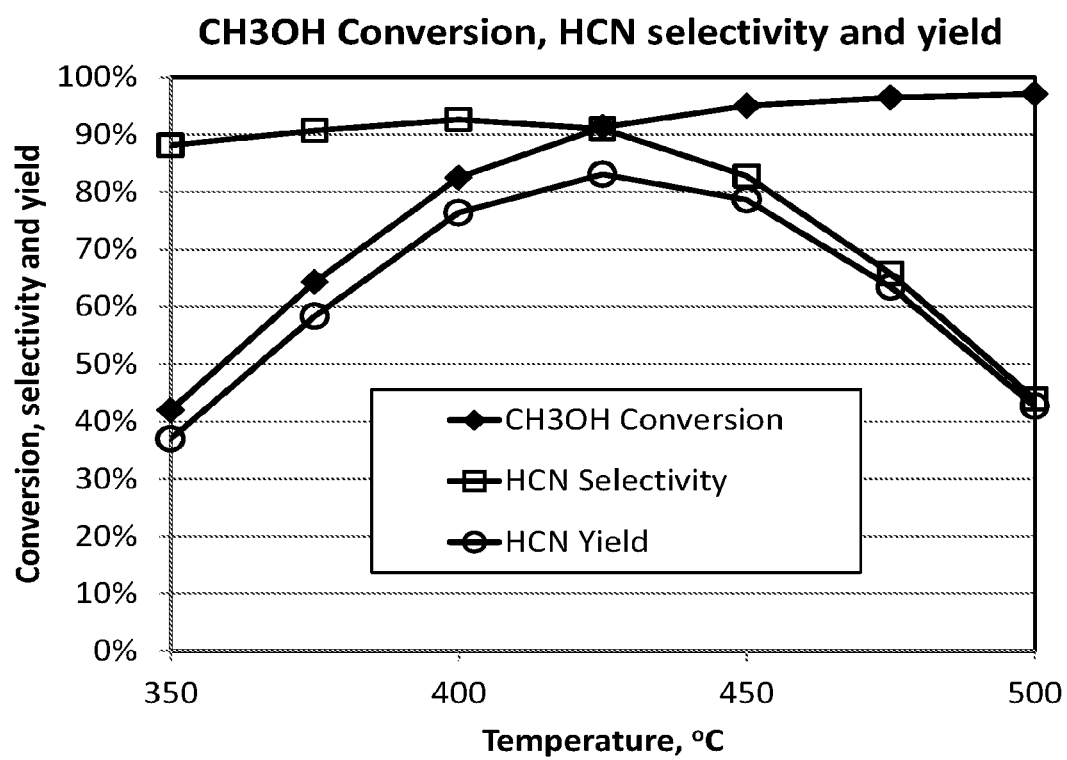
FIG. 5 illustrates the test results of a temperature optimization study described in Example 13 using catalyst composition E1 which shows a maximum yield of HCN unexpectedly achieved at 425° C.

E1 catalyst was tested at 350° C., 375° C., 400° C., 425° C., 450° C., 475° C. and 500° C. and W/F=0.05 (g·s)/ml with a feed composition comprising $NH_3$ (7 vol. %), $CH_3OH$ (6.9 vol. %), and $O_2$ (13 vol. %) balanced with helium. The test results are shown in FIG. 5. The results showed that $CH_3OH$ conversion increased with temperature and HCN selectivity unexpectedly increased with temperature between 350° C. and 400° C. and started to decrease with temperatures above 400° C. The maximum yield of HCN is unexpectedly achieved at 425° C.

Example 14 ($CH_3OH$ and $NH_3$ Use Efficiencies of E1 Catalyst)

Figure 6A:
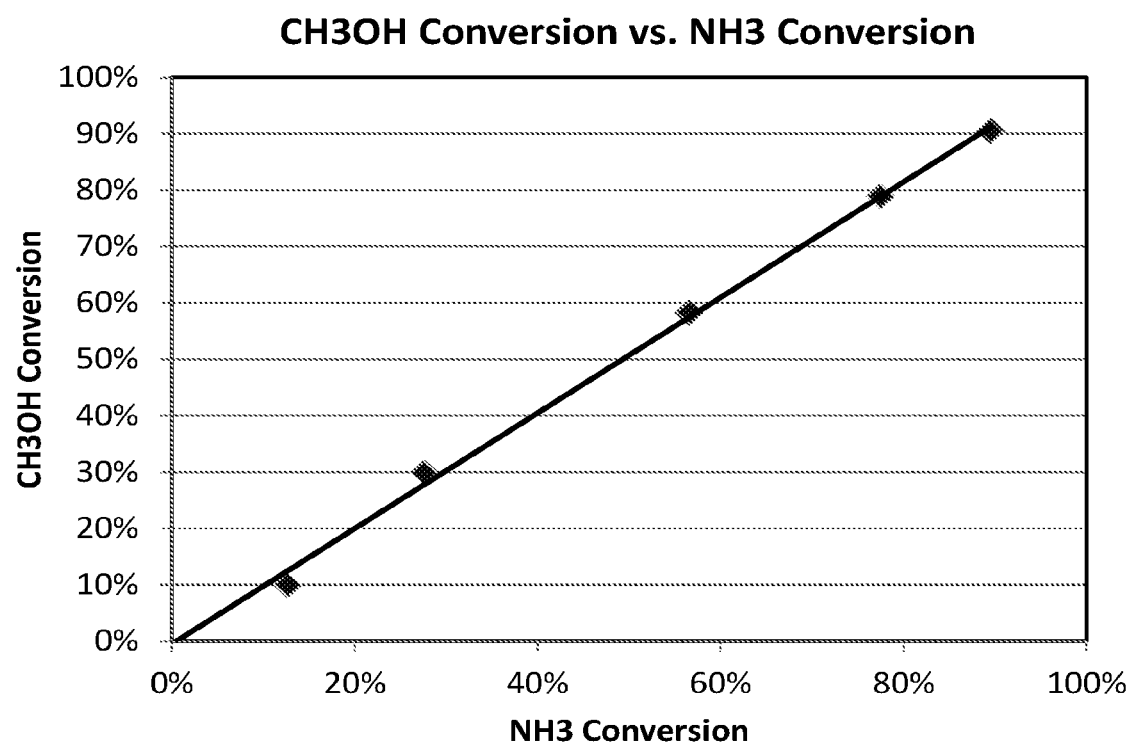
FIG. 6 illustrates that catalyst composition E1 provides a linear conversion fraction of $CH_3OH$ in a direct 1:1 proportion of $NH_3$ converted (FIG. 6A); and $NH_3$ and $CH_3OH$ use efficiencies (FIG. 6B) at various temperatures.
Figure 6B:
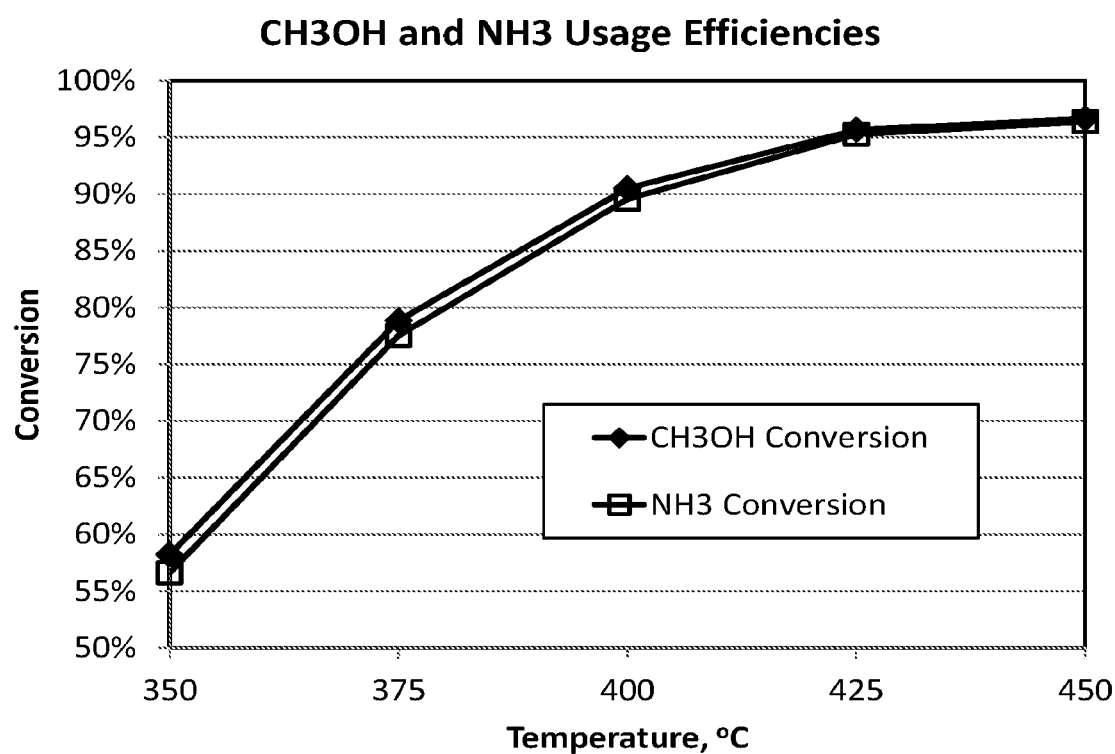

E1 catalyst was tested at a temperature from 350° C. to 450° C. and W/F=0.097 (g·s)/ml. The feed composition was $NH_3$ (7 vol. %), $CH_3OH$ (6.9 vol. %), $O_2$ (13 vol. %) and balanced with helium. The test results are shown in FIGS. 6A and 6B. The results also show a linear correlation between $CH_3OH$ and $NH_3$ conversion. Their usages are beyond 95% at temperature at and above 425° C.

Example 15 (E15, Coating E10 Catalyst onto a Monolith)

A standard 230 cpsi monolith of 6"×6" was core drilled into 1.5"×6" pieces. As described, approximately 1.32 kg of the E10 catalyst powder was added with 3.98 kg deionized water and ball-milled for 24 hrs to make slurry having solids content about 25% by weight. After each dip-coating, the excess liquid was removed by an air knife at 20 psi. The coated monolith was dried at 150° C. for 1 hr and finally calcined at 550° C. for 3 hrs to get sample. The above dip-coating and drying steps were repeated twice to eventually obtain a target catalyst loading of about 0.11 g/cc of monolith volume.

Example 16 (Simulated AN Reactor Effluent Test in Fixed-Bed Monolith Reactor)

A monolith coated per the process described in Example 15 was tested in a simulated AN reactor effluent containing 1% $CH_3OH$, 1% $NH_3$, 3% AN, 4% $O_2$ and the remainder $N_2$. The feed to this catalytic monolith reactor was set at 351° C. and 20 psig and a superficial space velocity of 4.1 $s^{-1}$ was maintained. Under these conditions, a 99.8% $CH_3OH$ conversion and 97.1% $NH_3$ conversion was achieved along with, 88.6% HCN yield and negligible AN burning.

Example 17 ($NH_3$ Destruction in the Absence of $CH_3OH$ in Fixed-Bed Monolith Reactor)

The monolith and the test conditions in Example 16 were repeated, except at 405° C. inlet and without the $CH_3OH$ in the feed. The feed composition for this test was 1% $NH_3$, 4% AN, 4% $O_2$ and balanced with $N_2$ at 377, 405, and 430° C. and 19.4 psig. Under these conditions, $NH_3$ conversions of 78% at 377° C. and 100% at 405 and 430° C. are achieved with negligible AN burning. Neither significant nor detectable amount of $NO_x$ and $N_2O$ is produced. Most of the $NH_3$ was expected to be oxidized to $N_2$ and water. The results are listed in Table 3.

TABLE 3

Ammonia destruction in $AN/O_2$ and in $O_2$ flow balanced with $N_2$

| Test | Feed | Temperature (° C.) | $NH_3$ conversion | AN burning |
|---|---|---|---|---|
| Example 17 | 1% $NH_3$, 4% AN, 4% $O_2$ | 377 | 78% | negligible |
| Example 17 | 1% $NH_3$, 4% AN, 4% $O_2$ | 405 | 100% | negligible |
| Example 17 | 1% $NH_3$, 4% AN, 4% $O_2$ | 430 | 100% | negligible |
| Example 18 | 1% $NH_3$, 4% $O_2$ | 398 | 100% | Not applicable |

Example 18 ($NH_3$ Destruction in $O_2$ in Fixed-Bed Monolith Reactor)

The monolith and the test conditions in Example 17 were repeated, except at a 398° C. inlet and without the AN in the feed. The feed composition for this test was 1% $NH_3$, 4% $O_2$ and balanced with $N_2$ at 398° C. and 19.6 psig. Under these conditions, a 100% $NH_3$ conversion was achieved. Neither significant nor detectable amounts of $NO_x$ and $N_2O$ were produced. Most of the $NH_3$ was expected to be oxidized to $N_2$ and water. The results are listed in Table 3.

Example 19 (Simulated AN Reactor Effluent Test in Packed Fixed-Bed Reactor)

E10 catalyst was tested at 450° C. and W/F=0.025 (g·s)/ml. The tests were done with and without the presence of AN in the feed. The E10 was a calcined powder sample and not coated and/or applied on any other supports or carriers. The reactor feed and effluent compositions are listed in Table 4. There was only a slight change of CO and $CO_2$ concentrations in the effluent when AN was added to the reactor feed, indicating that AN was practically not oxidized in the process according to the current invention.

TABLE 4

Testing results of simulated AN reactor effluent in packed fixed-bed reactor

| | Feed and/or effluent product, % | | | | | | | $CH_3OH$ Conversion | HCN Selectivity | HCN Yield |
|---|---|---|---|---|---|---|---|---|---|---|
| | $CO_2$ | $NH_3$ | $CH_3OH$ | $O_2$ | HCN | CO | AN | | | |
| Feed | | 7.0 | 6.9 | 17.9 | | | | — | — | — |
| Effluent | 0.18 | 1.37 | 0.03 | 8.41 | 6.37 | 0.10 | 0.00 | 99.58% | 95.80% | 95.40% |
| Feed | | 7.0 | 6.9 | 17.9 | | | 0.79 | — | — | — |
| Effluent | 0.20 | 2.09 | 0.02 | 10.48 | 5.14 | 0.05 | 0.79 | 99.56% | 95.24% | 94.82% |

Example 20 (Unexpected High Activity and Selectivity on E12)

Figure 7:
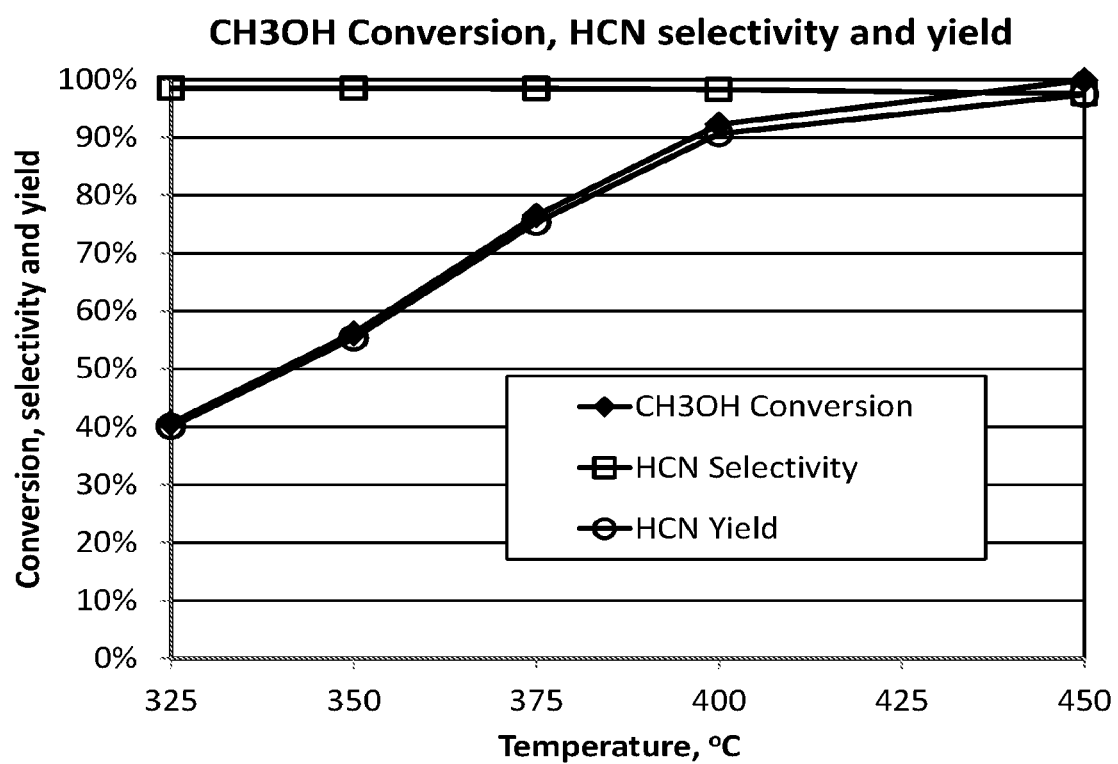
FIG. 7 illustrates test results indicating that catalyst composition E12 achieves an unexpectedly high conversion (approximately 97% to 100%) of injected $CH_3OH$ into HCN for all runs performed at 425° C. or above.

E12 catalyst was tested at a temperature from 325° C. to 450° C., W/F=0.0083 (g·s)/ml, and a feed composition of $NH_3$ (2.8 vol. %), $CH_3OH$ (1.49 vol. %), $O_2$ (4.97 vol. %), AN (2.18 vol. %) balanced with helium. The results are shown in FIG. 7. The $CH_3OH$ conversion and HCN yield increase with increasing reaction temperature. About 90% HCN selectivity and yield were achieved at 400° C. and >97% at 450° C.

Example 21 (HCN Production from Propionitrile (PN) Ammoxidation on E12)

Figure 8:
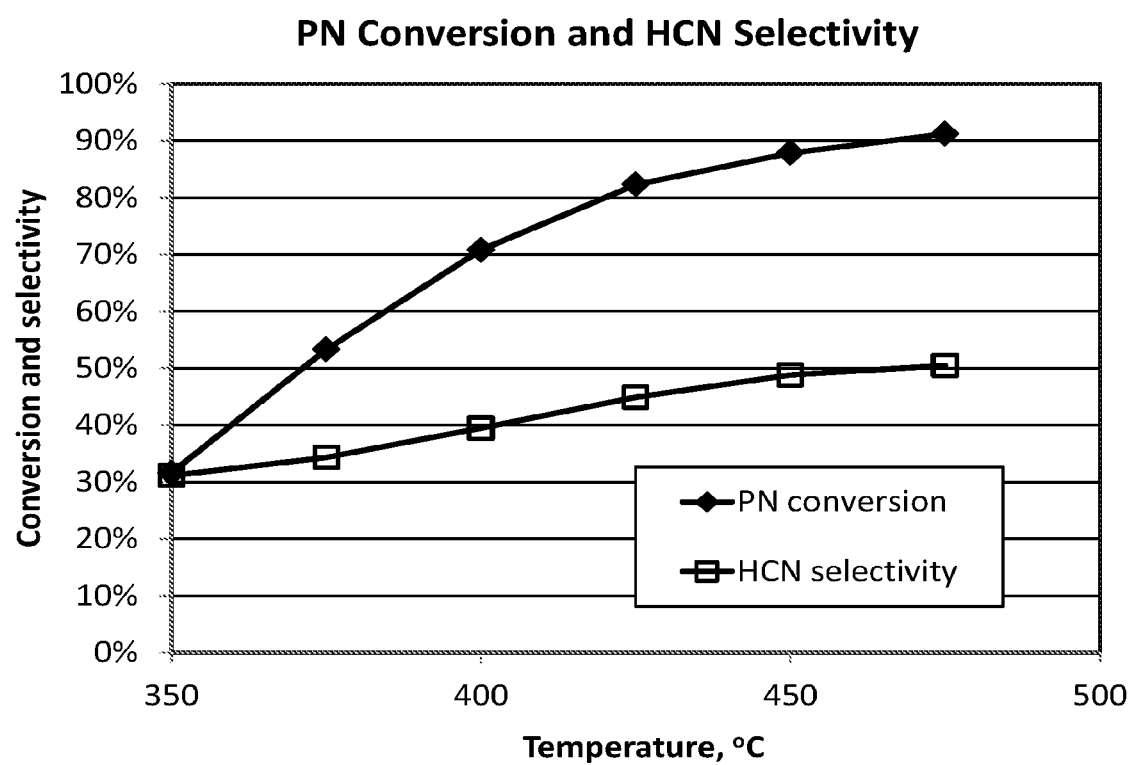
FIG. 8 illustrates the test results of HCN production from propionitrile (PN) ammoxidation using the catalyst composition E12.

E12 catalyst was tested at temperatures ranging from 350 to 475° C., W/F=0.2 (g·s)/ml, and a feed composition of $O_2$ (10.1 vol. %), $NH_3$ (6.10 vol. %), propionitrile (PN) (4.1 vol. %) balanced with helium. PN conversion is calculated using the following formula $$X_{PN}=(1-[PN]_{OUT}/[PN]_{IN})*100\%$$

where $[PN]_{IN}$ is the concentration of PN in the feed in vol. %, and $[PN]_{OUT}$ is the concentration of PN in the effluent in vol. %. Selectivity to HCN is calculated using the following formula $$S_{HCN}=([HCN]_{OUT}/([CO]_{OUT}+[CO2]_{OUT}+[HCN]_{OUT}+2*[PN]_{OUT}))*100\%$$

where $[CO]O_{UT}$, $[CO2]_{OUT}$, $[HCN]O_{UT}$ and $[PN]O_{UT}$ are concentrations (vol. %) in the reactor effluent. The results of the tests are shown in FIG. 8.

Example 22 (HCN and ACN Production from EtOH Ammoxidation)

Figure 9:
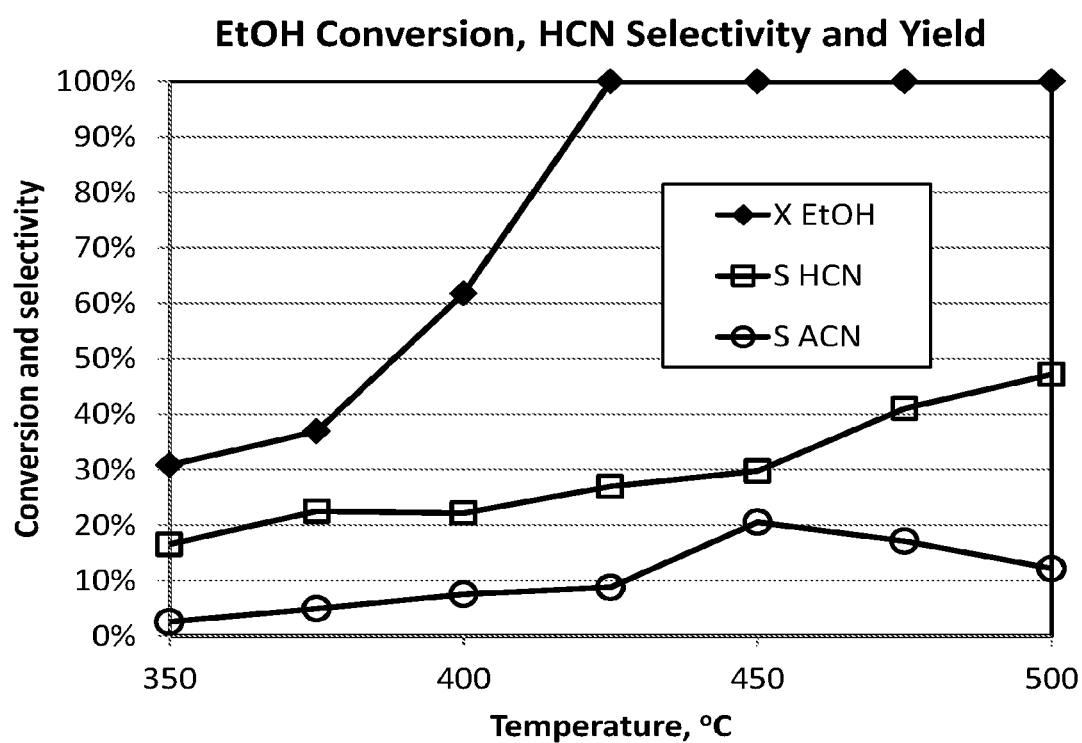
FIG. 9 illustrates the test results of HCN and ACN formation from EtOH ammoxidation using the catalyst composition E12.

E12 catalyst was tested at temperatures ranging from 350 to 500° C. at W/F=0.2 (g·s)/ml. The composition of the feed was $O_2$ (9.6 vol. %), $NH_3$ (6.17 vol. %), EtOH (7 vol. %). EtOH conversion was calculated using the following formula $$X_{EtOH}=(1-[EtOH]_{OUT}/[EtOH]_{IN})*100\%$$

where $[EtOH]_{IN}$ is the concentration of EtOH in the feed in vol. %, and $[EtOH]_{OUT}$ is the concentration of EtOH in the effluent in vol. %. Selectivity to HCN and ACN is calculated using the following formulas $$S_{HCN}=([HCN]_{OUT}/([CO]_{OUT}+[CO2]_{OUT}+[HCN]_{OUT}+2*[ACN]_{OUT}))*100\%$$

$$A_{ACN}=([ACN]_{OUT}/([EtOH]_{IN}-[EtOH]_{OUT}))*100\%$$

where $[CO]_{OUT}$, $[CO2]_{OUT}$, $[HCN]_{OUT}$ and $[ACN]_{OUT}$ are concentrations (vol. %) in the reactor effluent. The results of the tests are shown in FIG. 9. The results showed that EtOH is being converted to HCN and ACN.

Example 23 (HCN and ACN Production from Acetone Ammoxidation)

Figure 10:
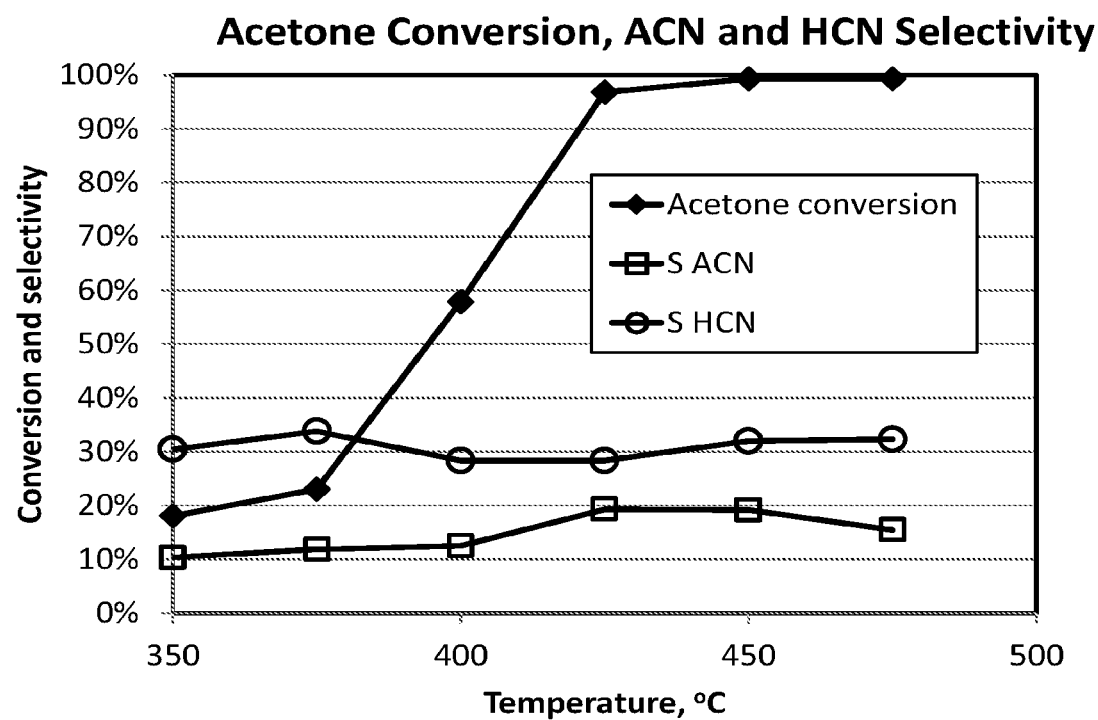
FIG. 10 illustrates the test results of HCN and ACN formation from acetone ammoxidation using the catalyst composition E12.

E12 catalyst was tested at temperatures ranging from 350 to 475° C. at W/F=0.2 (g·s)/ml. The composition of the feed was $O_2$ (9.6 vol. %), $NH_3$ (6.10 vol. %), and acetone (5.1 vol. %). Acetone conversion was calculated using the following formula $$X_{Acetone}=(1-[Acetone]_{OUT}/[Acetone]_{IN})*100\%$$

where $[Acetone]_{IN}$ is the concentration of Acetone in the feed in vol. %, and $[Acetone]_{OUT}$ is the concentration of Acetone in the effluent in vol. %. Selectivity to HCN and ACN is calculated using the following formulas $$S_{HCN}=([HCN]_{OUT}/([CO]_{OUT}+[CO2]_{OUT}+[HCN]_{OUT}+2*[ACN]_{OUT}))*100\%$$

$$S_{ACN}=(2*[ACN]_{OUT}/([CO]_{OUT}+[CO2]_{OUT}+[HCN]_{OUT}+2*[ACN]_{OUT}))*100\%$$

where $[CO]_{OUT}$, $[CO2]_{OUT}$, $[HCN]_{OUT}$ and $[ACN]_{OUT}$ are concentrations (vol. %) in the reactor effluent; ACN stands for acetonitrile. No products other than CO, $CO_2$, ACN and HCN were observed. The results of the tests are shown in FIG. 10. The results showed that acetone is being converted to HCN and ACN.

Results

The catalyst compositions of the present invention effectively convert unconverted $NH_3$ and $O_2$ present in a simulated AN reactor effluent stream to value-added product HCN, which is illustrated in FIG. 1 as in-line processing of the invention, and eliminate the need for the conventional process of $NH_3$ removal via acid neutralization. As described herein, the catalyst compositions and the ammoxidation process of the present invention can also be used to increase HCN and nitrile products, such as ACN in the AN reactor effluent via the introduction of alcohols such as EtOH and/or nitriles and/or ketones ammoxidation.

Figure 3:
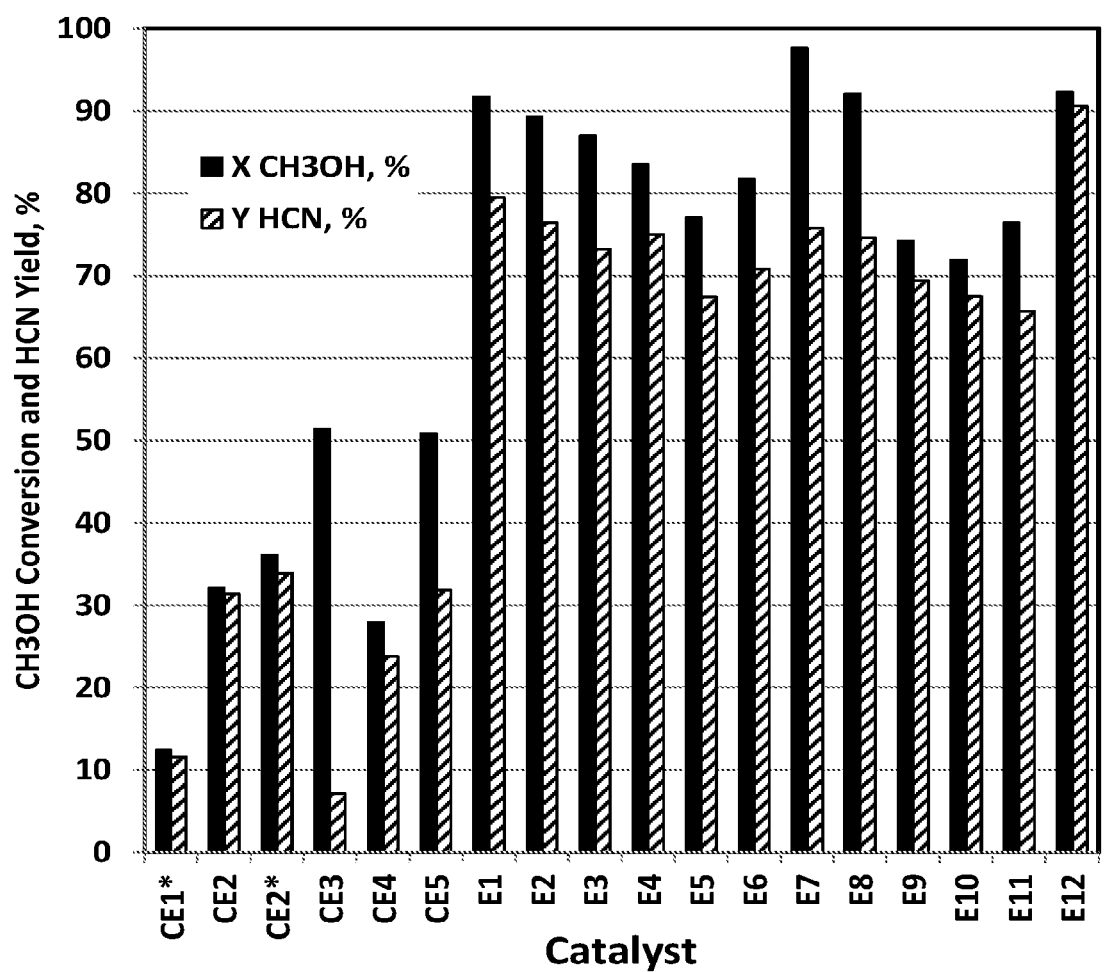
FIG. 3 illustrates the high performance of the ammoxidation catalyst compositions E1-E12 of the present invention in reacting with $CH_3OH$ to produce HCN in contrast with comparative catalysts CE1-CE5, where CE1 is a catalyst of $CH_3OH$ ammoxidation to produce HCN and CE2 is a catalyst of propylene ammoxidation.

As can be seen from FIG. 3 and Table 1, the novel catalyst compositions of the present invention exhibit higher $CH_3OH$ and $NH_3$ conversions, and HCN selectivity and yield under $CH_3OH$ ammoxidation conditions compared to similar comparative catalyst compositions. A continued DOE approach or similar methodology as shown in FIG. 2 beyond the elemental composition ranges listed in Table 5 of the conducted DOE studies or any additional modifications and variations to the composition in Table 5 could be made thereto without departing from the scope of the present invention. FIGS. 4A and 4B show comparable $CH_3OH$ conversions and HCN yields at both high and low Mo/Fe molar ratios, indicating the molybdenum usage from various source compounds may be further optimized and/or varied to achieve improved performance.

TABLE 5

Elemental composition ranges of DOE studies

| Element | Minimum at Fe = 1 | Maximum at Fe = 1 |
| --- | --- | --- |
| Mo | 2.17 | 47.97 |
| Bi | 0.127 | 0.127 |
| Cr | 0.074 | 0.074 |
| Fe | 1 | 1 |
| Ni | 0 | 2.89 |
| Cu | 0 | 2.89 |
| Zn | 0 | 2.89 |
| Co | 0 | 2.89 |
| Mn | 0 | 0.26 |
| Sn | 0 | 1.22 |
| Sb | 0 | 0.76 |
| Gd | 0 | 2.00 |
| Mg | 0 | 1.17 |
| Re | 0 | 0.26 |
| Ce | 0 | 2.81 |
| Ru | 0 | 1.00 |
| Ti | 0 | 14.64 |
| Zr | 0 | 6.39 |
| Al | 0 | 12.73 |
| Si | 0 | 47.22 |

Table 2 illustrates that an unsupported catalyst provides high HCN yield and supports incorporation such as $TiO_2$ and high surface area $SiO_2$ into the catalyst to further increase $CH_3OH$ conversion and HCN yield. Therefore, the catalysts of the present invention can perform with or without a support. If needed, suitable supports include, but are not limited to, silica, zirconia, titania, alumina and mixtures thereof.

An optimization study is illustrated in FIG. 5 in which $CH_3OH$ conversion increases with increasing temperature but HCN selectivity remains almost unchanged from 350 to 425° C. A maximum yield of HCN is unexpectedly achieved at 425° C. Similarly, other reaction conditions, such as pressure, space velocity, linear velocity, and residence time can also be optimized to achieve higher product yields from ammoxidation processing of alcohols and/or nitriles to HCN, ACN, and/or to corresponding nitriles employing the catalyst compositions of the present invention.

The $CH_3OH$ and $NH_3$ usage efficiencies as shown in in FIG. 6 clearly indicate a linear correlation between $CH_3OH$ conversion and $NH_3$ conversion, nearly a 1:1 reaction efficiency. In addition to observed high HCN selectivity, low energy consumption (due to hot effluent transferring heat to the process in the invention), and ammonia sulfate waste avoidance, the catalyst compositions of the present invention promote a high material usage efficiency, low energy and an environmentally benign ammoxidation process.

Table 3 indicates that AN burnings are negligible in the fixed-bed catalytic monolith reactor using the catalyst of the present invention. AN burning or destruction is not desirable in the $CH_3OH$ ammoxidation process of the present invention as described above. The results clearly indicate that an AN product present in the AN production reactor effluent was not destroyed, burned, and/or damaged in the subsequent $CH_3OH$ ammoxidation process of the present invention. Additionally, $NH_3$ present in the $NH_3/AN/O_2/N_2$ feed is fully (100%) converted to $N_2$ at 405° C. and 430° C. in the absence of $CH_3OH$. These interesting results indicate that the catalysts of the present invention can completely oxidize $NH_3$ to $N_2$ without burning AN present in the feed. Practically speaking, the catalysts of the present invention can convert unconverted $NH_3$ in the AN reactor effluent to $N_2$ without burning AN present in the feed, thus avoiding the unconverted $NH_3$ neutralization by acid and subsequent separation and disposal as conventionally practiced. Furthermore, $NH_3$ present in the $NH_3/O_2/N_2$ feed is also fully (100%) converted to $N_2$ at 398° C. in the absence of $CH_3OH$ and AN. These results suggest that the catalyst compositions of the present invention can also completely and selectively oxidize $NH_3$ to only $N_2$ in $O_2/N_2$, an oxygen-rich environment. As such, the catalysts of the present invention can also be employed in the removal of $NH_3$ from industrial effluents such as mobile exhaust sources (including automobiles and trucks) and stationary exhaust sources (including power plants) at a significantly lower cost than existing noble metal catalysts, such as Pt-based catalysts. In addition to negligible AN burning using the catalyst-coated monolith as shown in Table 3, the results of using catalyst powder, illustrated in Table 4 not only confirm the lack of detectable amounts of AN burning but also reveal that the $CH_3OH$ conversion and HCN selectivity and yield are almost unchanged and/or not impacted by AN present in the feed.

The results shown in FIG. 7 depict high $CH_3OH$ conversion and unexpectedly high (close to 100%) HCN selectivity at any temperature between 325° C. to 450° C. This observation illustrates the fact that high catalyst activity and high HCN selectivity is unexpected and could not have been predicted by those skilled in the art. As shown in FIGS. 8-10, the HCN and HCN/ACN can be produced from propionitrile (PN), EtOH, and acetone ammoxidation, respectively, using the catalysts of the present invention. The HCN selectivity from PN and the HCN/ACN selectivity from EtOH and acetone ammoxidation are acceptable but can be further increased via optimization of the catalyst compositions and the testing conditions. The relative amounts of HCN and ACN can be controlled by the process of the present invention as shown in FIG. 1 via using a mixture of alcohols with varying ratios of $CH_3OH$ to EtOH. An increase in HCN and ACN production during the production of AN can be achieved using alcohol mixtures. In further similarly conducted tests, the ammoxidation of alcohols and/or nitriles and/or ketones to HCN and/or to corresponding nitriles can be achieved using the catalyst compositions and/or processes of the present invention.

In addition to unconverted $NH_3$ and/or $O_2$ present in an effluent stream of a primary AN reactor, there are also additional components, such as PN, ACN, acrolein, and methacrylonitrile, present as process by-products. AN burning is negligible in multiple exemplary embodiments. PN reacted with $NH_3$ in Example 21 to produce HCN suggests that additional components in the reactor effluent are capable of reacting with unconverted $NH_3$ and/or $O_2$ to produce additional HCN and/or nitriles in the presence of the catalyst compositions of the present invention in the secondary reactor outside the primary AN reactor. These additional organic compound components, present as by-products from primary ammoxidation reactor effluent, can also be provided independently. Additional organic compound components include propane present as an impurity of a propylene feed or as a co-feed with propylene to a primary AN reactor. This unconverted propane and/or propylene can react with unconverted $NH_3$ and/or $O_2$ to produce additional HCN and AN in the presence of the catalyst compositions of the present invention and/or suitable ammoxidation catalysts in the secondary reactor outside the primary AN reactor. These additional components present in an unconverted feed such as propylene/propane and isobutylene/isobutane from a primary ammoxidation reactor effluent can also be provided independently. Therefore, when $CH_3OH$ is injected into the secondary reactor outside the primary ammoxidation reactor, the unconverted $NH_3$ and/or $O_2$ react with both the injected $CH_3OH$ and with any additional organic compound components present in the ammoxidation reactor effluent (or provided independently) to produce additional HCN and nitriles. When an alcohol or alcohol-containing mixture, a nitrile or nitrile-containing mixture, a ketone or ketone-containing mixture, an aldehyde or aldehyde-containing mixture, a carboxylic acid or carboxylic acid-containing mixture, an ester or ester-containing mixture, an ether or ether-containing mixture, their derivatives, or mixtures thereof is injected into the secondary reactor, the unconverted $NH_3$ and/or $O_2$ present in an effluent stream of the primary ammoxidation reactor react with both (i) injected organic compound components and (ii) any additional organic compound components (such as unconverted alkanes, alkenes, aromatics, alcohols, aldehydes, their derivatives, including nitriles and/or mixtures thereof) present in the reactor effluent (or provided independently) to produce additional HCN and nitriles.

Although the present invention has been disclosed in terms of selected embodiments, it will be apparent to one of ordinary skill in the art that changes and modifications may be made to the invention without departing from its spirit or scope as set forth herein. All patents and other publications referred to herein are incorporated by reference in their entireties.

The invention claimed is:

1. A catalyst composition comprising a mixed oxide catalyst of formula $$Fe Mo_i Cr_j Bi_k M_m N_n Q_q X_x Y_y O_r \quad (II)$$

wherein in the formula (II):
M is Ce and/or Sb;
N is La, Pr, Nd, Pm, Sm, Eu, Gd, Tb, Dy, Ho, Er, Tm, Yb, Lu, Ti, Zr, Hf, B, Al, Ga, In, Tl, Si, Ge, Sn, Pb, P, and/or As;
Q is Ru, and/or Os;
X is Co, Rh, Ir, Ni, Pd, Pt, Cu, Ag, Au, Zn, Cd, Hg, Mn, Re, V, Nb, Ta, Se, and/or Te;
Y is an alkaline earth metal and/or an alkali metal;
$0.2 \leq i \leq 100$;
$0 \leq j \leq 2$;
$0 \leq k \leq 2$;
$0.05 \leq m \leq 10$;
$0 \leq n \leq 200$;
$0 < q \leq 8$;
$0 \leq x \leq 30$;
$0 \leq y \leq 8$;
j and k<i;
m>j; and
r is the number of oxygen atoms required to satisfy the valence requirements of the component elements other than oxygen present in formula (II),
wherein:
$4 \leq m+n+q+x+y \leq 200$;
$0 < q+x+y \leq 30$; and
wherein the catalyst composition has a surface area of from 2 to 500 m2/g as determined by the Brunauer-Emmett-Teller (BET) method.

2. The catalyst composition according to claim 1, wherein in the formula (II):
$0.3 \leq i \leq 50$;
$0 \leq j \leq 1.5$;
$0 \leq k \leq 1.5$;
$0.1 \leq m \leq 8$;
$0 \leq n \leq 100$;
$0 < q \leq 3$;
$0 \leq x \leq 10$;
$0 \leq y \leq 3$;
j and k<i;
m>j;
$4.5 \leq m+n+q+x+y \leq 100$;
$0 < q+x+y \leq 10$.

3. The catalyst composition according to claim 2, wherein in the formula (II):
$0.5 \leq i \leq 50$;
$0 \leq j \leq 0.5$;
$0 \leq k \leq 0.75$;
$0.2 \leq m \leq 5$;
$0 \leq n \leq 60$;
$0 < q \leq 1.5$;
$0 \leq x \leq 5$;
$0 \leq y \leq 2$;
j and k<i;
m>j;
$5 \leq m+n+q+x+y \leq 60$; and
$0 < q+x+y \leq 7.5$.

4. The catalyst composition according to claim 1, wherein the catalyst composition consists of a mixed oxide catalyst of the formula (II) and a support.

5. The catalyst composition according to claim 1, wherein the catalyst composition further comprises a support selected from the group consisting of silica, zirconia, titania, alumina and mixtures thereof.

6. The catalyst composition according to claim 5, wherein the support comprises between 20 and 80 weight percent by weight of the catalyst composition.

7. The catalyst composition according to claim 5, wherein the support is colloidal silica having an average particle size ranging from approximately 2 to 1,000 nm in diameter.

8. The catalyst composition according to claim 5, wherein the catalyst composition is in a form selected from the group consisting of spheres, granules, pellets, extrudates, cylinders, trilobes, quadrilobes, ribs, rings, monoliths, wagon wheels, gauzes and mixtures thereof.

9. The catalyst composition according to any claim 5, wherein the catalyst composition is coated onto a monolith structure.

10. The catalyst composition according to claim 9, wherein the monolith is selected from the group consisting of cordierite, a ceramic, a metal, a zeolite, a carbide, mullite, alumina, a clay, carbon and mixtures thereof.

11. The catalyst composition according to claim 1, wherein the catalyst composition consists of a mixed oxide catalyst of the formula (II) and a support.

12. The catalyst composition according to claim 1, wherein the ratio of Fe to Mo is 1:48.

13. The catalyst composition according to claim 1, wherein in the formula (II):
M is Sb;
N is La, Pr, Nd, Pm, Sm, Eu, Gd, Tb, Dy, Ho, Er, Tm, Yb, Lu, and/or Si;
Q is Ru;
X is Co; and
Y is Mg.

14. The catalyst composition according to claim 1, wherein in the formula (II):
M is Ce and Sb;
N is La, Pr, Nd, Pm, Sm, Eu, Gd, Tb, Dy, Ho, Er, Tm, Yb, Lu, Si, and/or Sn;
Q is Ru;
X is Ni and Re; and
Y is an alkaline earth metal and/or an alkali metal, wherein y is 0.

15. The catalyst composition according to claim 1, wherein in the formula (II):
M is Ce;
N is Si;
Q is Ru;
X is Mn and Re;
Y is an alkaline earth metal and/or an alkali metal, wherein y is 0.

16. The catalyst composition according to claim 1, wherein in the formula (II):
M is Sb;
N is Si;
Q is Ru;
X is Ni, Zn, and Re;
Y is Mg.

* * * * *